(12) United States Patent
Tougan et al.

(10) Patent No.: US 12,174,118 B2
(45) Date of Patent: Dec. 24, 2024

(54) BLOOD ANALYZER

(71) Applicants: SYSMEX CORPORATION, Kobe (JP); OSAKA UNIVERSITY, Suita (JP)

(72) Inventors: Takahiro Tougan, Osaka (JP); Yuji Toya, Kobe (JP)

(73) Assignees: SYSMEX CORPORATION, Kobe (JP); OSAKA UNIVERSITY, Osaka (JP)

( * ) Notice: Subject to any disclaimer, the term of this patent is extended or adjusted under 35 U.S.C. 154(b) by 412 days.

(21) Appl. No.: 17/228,220

(22) Filed: Apr. 12, 2021

(65) Prior Publication Data
US 2021/0318240 A1 Oct. 14, 2021

(30) Foreign Application Priority Data

Apr. 13, 2020 (JP) .................................. 2020-071704

(51) Int. Cl.
*G01N 21/64* (2006.01)
*G01N 1/31* (2006.01)
(Continued)

(52) U.S. Cl.
CPC .......... *G01N 21/6428* (2013.01); *G01N 1/31* (2013.01); *G01N 21/49* (2013.01); *G16H 10/40* (2018.01);
(Continued)

(58) Field of Classification Search
CPC ...... G01N 1/31; G01N 15/12; G01N 15/1459; G01N 2015/0073; G01N 2015/1486;
(Continued)

(56) References Cited

U.S. PATENT DOCUMENTS 8,541,561 B2   9/2013 Ban et al.
10,113,966 B2  10/2018 Yamada et al.
(Continued)

FOREIGN PATENT DOCUMENTS

CN   105388100 A   3/2016
CN   106483109 A   3/2017
(Continued)

OTHER PUBLICATIONS

"Guideline: Daily Iron Supplementation in Infants and Children", World Health Organization, 2016, 54 pages, Retrieved from the Internet: URL:https://www.who.int/nutrition/publications/micronutrients/guidelines/daily_iron_supp_childrens/en/.
(Continued)

*Primary Examiner* — Dennis White
(74) *Attorney, Agent, or Firm* — Crowell & Moring LLP

(57) ABSTRACT

Disclosed is a blood analyzer including: a first sample preparation unit configured to prepare, from a blood sample, a first measurement sample for measuring a red blood cell infected with malaria; a second sample preparation unit configured to prepare, from the blood sample, a second measurement sample for measuring intrinsic fluorescence of a red blood cell; a light source unit configured to apply light to the first and the second measurement samples; a detection unit configured to detect fluorescence and scattered light generated from the first measurement sample to which light has been applied, and detect intrinsic fluorescence generated from the second measurement sample to which light has been applied; and an information processing unit configured to generate information about malaria infection based on fluorescence and scattered light detected from the first measurement sample, and generate information about iron-deficiency anemia based on intrinsic fluorescence detected from the second measurement sample.

20 Claims, 24 Drawing Sheets

(51) Int. Cl.
  *G01N 21/49* (2006.01)
  *G16H 10/40* (2018.01)
  *G16H 40/63* (2018.01)
  *G16H 50/30* (2018.01)
(52) U.S. Cl.
  CPC ............. *G16H 40/63* (2018.01); *G16H 50/30* (2018.01); *G01N 2021/6439* (2013.01)
(58) Field of Classification Search
  CPC ........... G01N 2021/6439; G01N 21/49; G01N 21/534; G01N 21/6428; G01N 21/6486; G01N 2333/445; G01N 21/6402; G01N 33/49; G01N 10/40; Y02A 50/30; Y02A 90/10; G16H 50/30; G16H 10/40; G16H 40/63
  See application file for complete search history.

(56) References Cited

U.S. PATENT DOCUMENTS

| | | | |
|---|---|---|---|
| 10,118,958 B2 | 11/2018 | Mueller et al. | |
| 10,822,403 B2 | 11/2020 | Mueller et al. | |
| 2008/0241911 A1 | 10/2008 | Ueno et al. | |
| 2013/0171681 A1* | 7/2013 | Shibata | G01N 1/10 435/29 |
| 2016/0061732 A1* | 3/2016 | Yamada | G01N 33/80 435/288.7 |
| 2016/0282377 A1* | 9/2016 | Nagai | G01N 27/08 |
| 2017/0059486 A1* | 3/2017 | Suzuki | G01N 33/4915 |
| 2017/0360075 A1 | 12/2017 | Connor et al. | |
| 2018/0188277 A1* | 7/2018 | Masuda | G01N 15/12 |

FOREIGN PATENT DOCUMENTS

| | | |
|---|---|---|
| EP | 2293062 B1 | 1/2015 |
| EP | 2990802 A1 | 3/2016 |
| EP | 3136081 A1 | 3/2017 |
| JP | 2008-241672 A | 10/2008 |

OTHER PUBLICATIONS

Extended European Search Report in Europe Application No. 21163161.9, dated Sep. 6, 2021, 8 pages.
M. Gwamaka et al., "Iron Deficiency Protects Against Severe Plasmodium falciparum Malaria and Death in Young Children", Clinical Infectious Diseasees, Feb. 21, 2012, vol. 54, No. 8, pp. 1137-1144, DOI:10.1093/cid/cis010, 8 pages.
Office Action in Japan Application No. 2020-071704, dated Dec. 26, 2023, 2 pages.
Office Action in Chinese Application No. 2021103872670.0, dated Sep. 9, 2024 (8 pages).

\* cited by examiner

FIG. 4
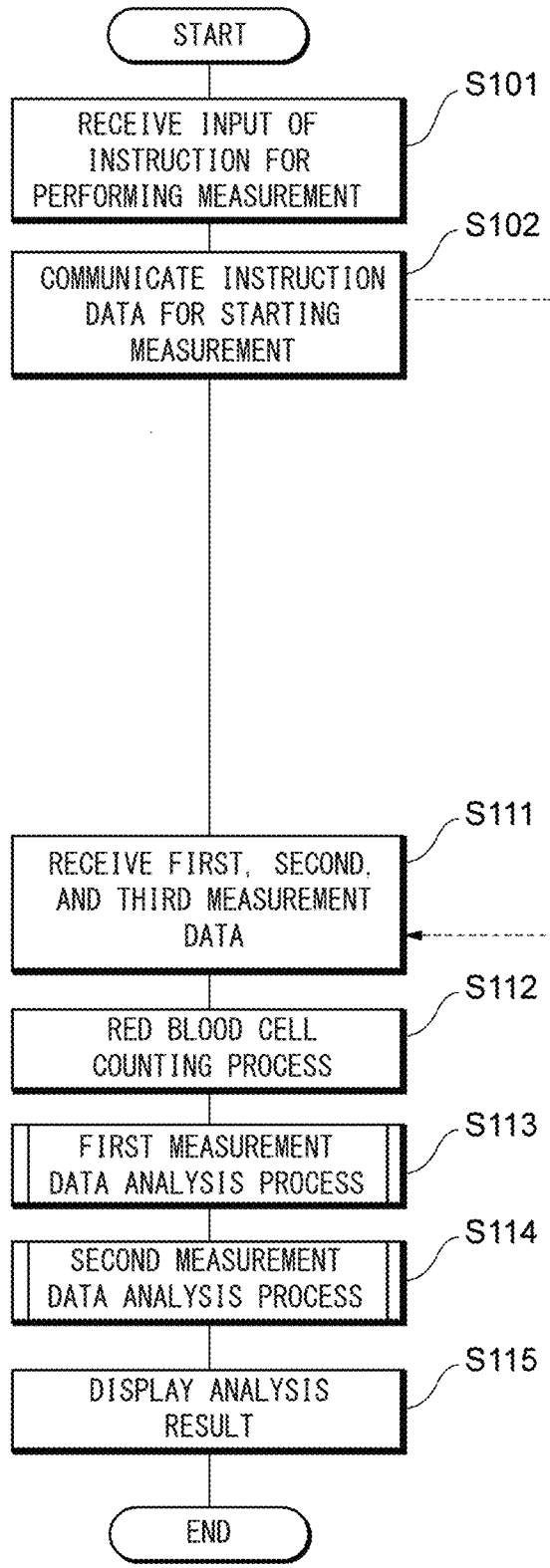
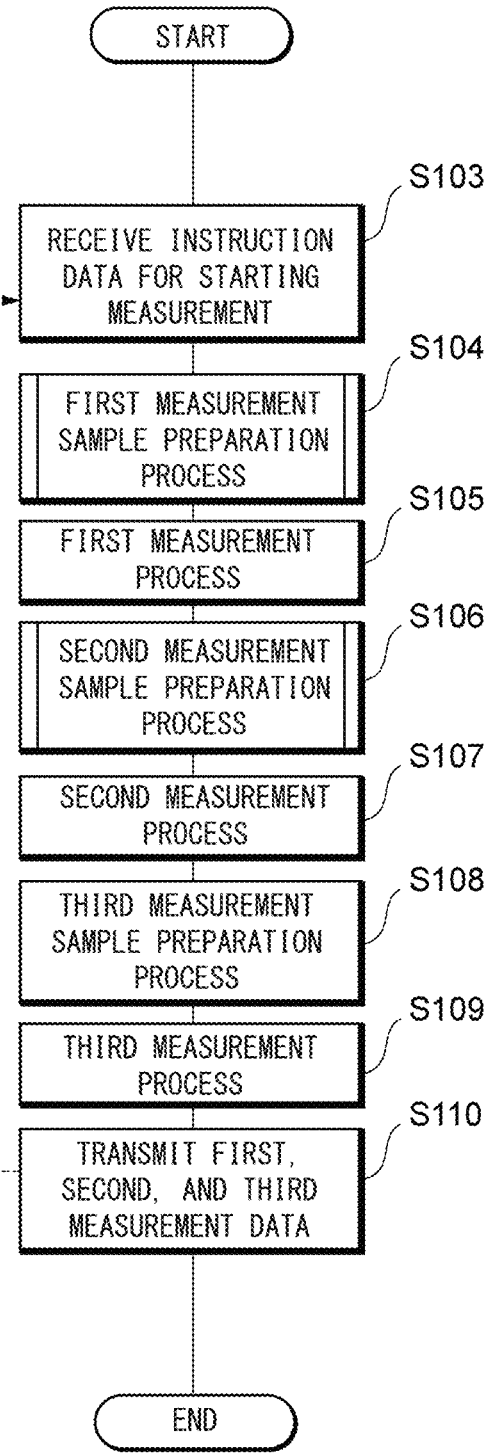

FIG. 18

| | IRON-DEFICIENCY ANEMIA DETERMINATION FLAG 0 | IRON-DEFICIENCY ANEMIA DETERMINATION FLAG 1 |
|---|---|---|
| MALARIA SPECIES/STAGE DETERMINATION FLAG 0 | NO MESSAGE | Iron deficiency? |
| MALARIA SPECIES/STAGE DETERMINATION FLAG 1 | P.falciparum? | Iron deficiency?<br>Malaria & Iron alert |
| MALARIA SPECIES/STAGE DETERMINATION FLAG 2 | P.falciparum+ | Iron deficiency?<br>Malaria & Iron alert |
| MALARIA SPECIES/STAGE DETERMINATION FLAG 3 | O. Malaria? | Iron deficiency?<br>Malaria & Iron alert |
| MALARIA SPECIES/STAGE DETERMINATION FLAG 4 | O. Malaria+ | Iron deficiency?<br>Malaria & Iron alert |

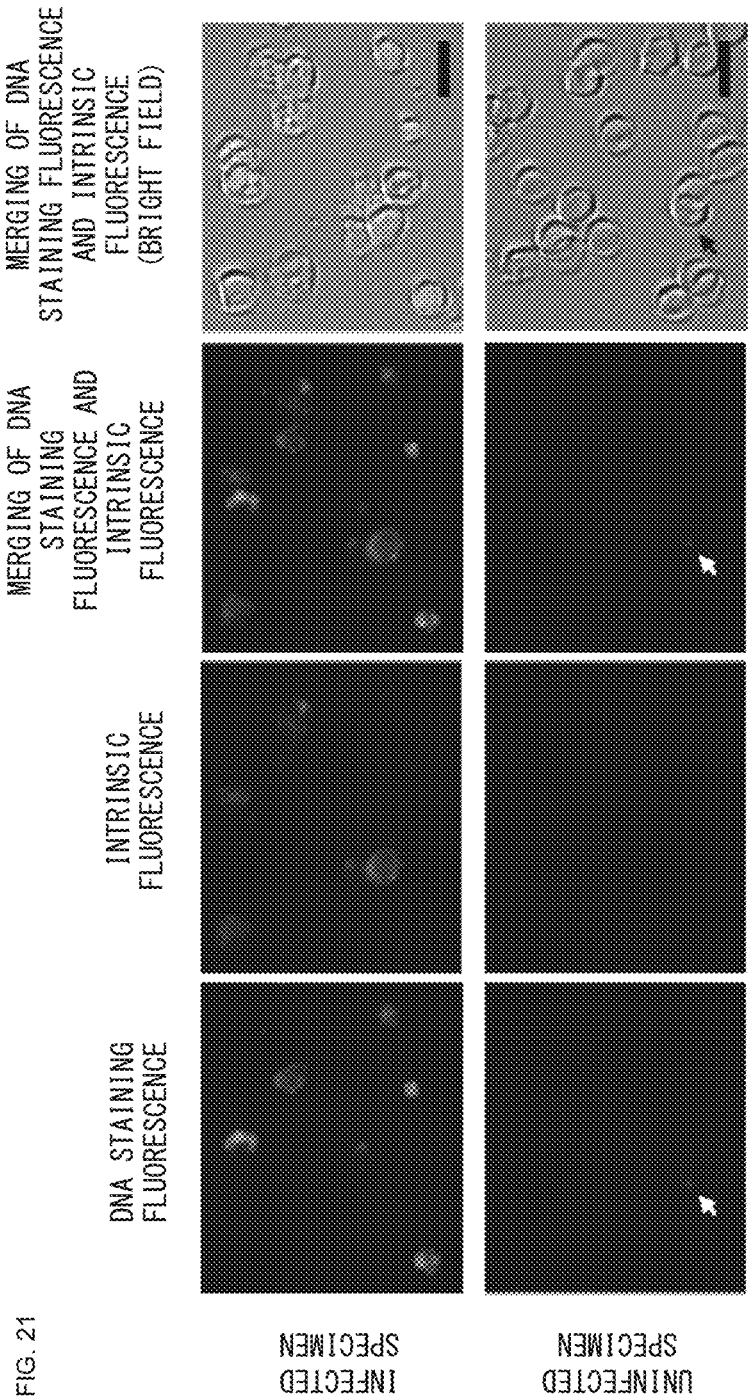

BLOOD ANALYZER

RELATED APPLICATIONS

This application claims priority to Japanese Patent Application No. 2020-071704, filed on Apr. 13, 2020, the entire content of which is incorporated herein by reference.

BACKGROUND OF THE INVENTION

1. Field of the Invention

The present invention relates to a blood analyzer.

2. Description of the Related Art

*Plasmodium* feeds on heme iron to grow. Therefore, if a doctor administers iron preparation to an iron-deficiency anemia patient infected with malaria without noticing the malaria infection, symptoms of the malaria may be aggravated. Accordingly, the World Health Organization (WHO) recommends that iron preparation be supplied to an iron-deficiency anemia patient together with diagnosis of malaria in malaria-endemic areas (for example, see "Guideline: Daily Iron Supplementation In Infants And Children," World Health Organization, 2016). The diagnosis of malaria is performed by detecting, for example, a DNA aptamer that specifically binds to pLDH (plasmodium lactate dehydrogenase) (for example, see Japanese Laid-Open Patent Publication No. 2012-254074). A DNA aptamer amplified by polymerase chain reaction (PCR) is fluorescently labeled, and fluorescence caused by excitation is detected, whereby the DNA aptamer is detected. Meanwhile, diagnosis of iron-deficiency anemia is performed by detecting, for example, an antibody bound to a repulsive guidance molecule (repulsive guidance molecule c) (for example, see PCT International Application Publication No. 2015-502753). The antibody is detected by enzyme-linked immunosorbent assay (ELISA).

As described above, for diagnosis of malaria, a DNA aptamer needs to be amplified by polymerase chain reaction to detect fluorescence caused by excitation. Meanwhile, for diagnosis of iron-deficiency anemia, a specific antibody needs to be bound to detect the antibody by enzyme-linked immunosorbent assay. Therefore, it has been required to separately prepare an analyzer for diagnosis of malaria and an analyzer for diagnosis of iron-deficiency anemia, and collect a sample for each of the analyzers and measure each sample, in order to determine whether or not iron preparation is to be supplied to an iron-deficiency anemia patient.

SUMMARY OF THE INVENTION

The scope of the present invention is defined solely by the appended claims, and is not affected to any degree by the statements within this summary.

According to an aspect of the present invention, a blood analyzer is provided, and the blood analyzer includes: a first sample preparation unit configured to prepare, from a blood sample, a first measurement sample for measuring a red blood cell infected with malaria; a second sample preparation unit configured to prepare, from the blood sample, a second measurement sample for measuring intrinsic fluorescence of a red blood cell; a light source unit configured to apply light to the first measurement sample and the second measurement sample; a detection unit configured to detect fluorescence and scattered light generated from the first measurement sample to which light has been applied, and detect intrinsic fluorescence generated from the second measurement sample to which light has been applied; and an information processing unit configured to generate information about malaria infection based on fluorescence and scattered light detected from the first measurement sample, and generate information about iron-deficiency anemia based on intrinsic fluorescence detected from the second measurement sample.

According to the present invention, one blood analyzer generates information for determining whether or not iron preparation is to be supplied to an iron-deficiency anemia patient. Therefore, measurement for determining whether or not iron preparation is to be supplied to an iron-deficiency anemia patient can be facilitated.

BRIEF DESCRIPTION OF THE DRAWINGS

FIG. 4 is a flow chart showing an operation of the blood analyzer according to the embodiment;

FIG. 18 illustrates a relationship between combinations of malaria species/stage determination flags and iron-deficiency anemia determination flags, and messages to be displayed;

FIG. 21 illustrates fluorescence microscope images of the peripheral blood of the malaria-infected mouse, according to the example.

DETAILED DESCRIPTION OF THE PREFERRED EMBODIMENTS

Figure 1:
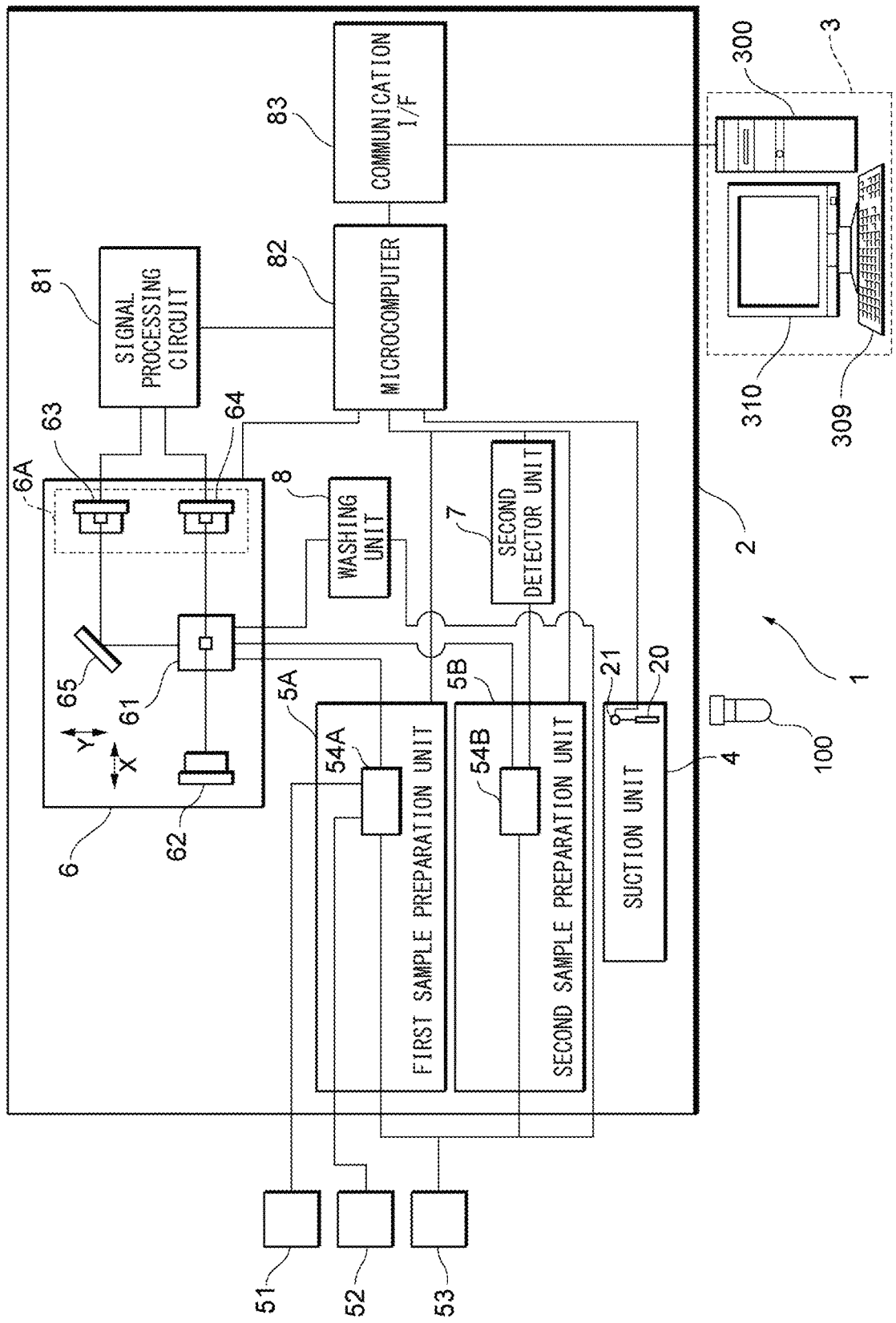
FIG. 1 is a schematic diagram illustrating a configuration of a blood analyzer according to an embodiment.

Hereinafter, an embodiment of the present disclosure will be described with reference to the drawings. In the following description for the drawings, the same or similar components are denoted by the same or similar reference characters. The drawings are schematic, and specific dimensions and the like need to be identified by referring also to the following description. It should be understood that relationship and proportion between dimensions may be different among the drawings.

In the present embodiment, a blood analyzer that determines whether or not malaria infection has occurred, based on intensities of fluorescence and scattered light generated by applying light to a first measurement sample prepared from a blood sample and a reagent, and that determines whether or not iron-deficiency anemia occurs, based on an intensity of intrinsic fluorescence from a red blood cell included in a second measurement sample prepared from the blood sample, will be described.

<Configuration of Blood Analyzer>

As shown in FIG. 1, the blood analyzer according to the embodiment includes a measurement unit 2 and an information processing unit 3. The measurement unit 2 takes in a blood sample, prepares first and second measurement samples from the blood sample, and performs optical measurement of the first and the second measurement samples. The information processing unit 3 processes first measurement data derived from the first measurement sample through measurement by the measurement unit 2 and second measurement data derived from the second measurement sample through the measurement, and outputs a result of analysis of the blood sample.

The measurement unit 2 includes a first sample preparation unit 5A that prepares, from a blood sample, the first measurement sample for measuring red blood cells that are infected with malaria, and a second sample preparation unit 5B that prepares, from a blood sample, the second measurement sample for measuring intrinsic fluorescence of red blood cells.

The measurement unit 2 further includes a suction unit 4. The suction unit 4 has a suction tube 20 and a metering unit 21, and suctions a blood sample stored in a test tube, through the suction tube 20.

The first sample preparation unit 5A has a first reaction chamber 54A, and is connected to reagent containers 51, 52, 53. The reagent container 51 stores a hemolyzing agent for contracting red blood cells. The reagent container 52 stores a nucleic acid staining reagent that contains a staining dye for staining nucleic acid such as DNA. The reagent container 53 stores a diluent that does not contain a hemolyzing agent and a staining dye.

The suction unit 4 moves the suction tube 20 to a portion above the first reaction chamber 54A and discharges the suctioned blood sample into the first reaction chamber 54A. The hemolyzing agent is sent from the reagent container 51 into the first reaction chamber 54A. The nucleic acid staining reagent is sent from the reagent container 52 into the first reaction chamber 54A. The blood sample, the hemolyzing agent, and the nucleic acid staining reagent are mixed in the first reaction chamber 54A. Furthermore, the diluent is sent from the reagent container 53 into the first reaction chamber 54A, and a reaction solution of the blood sample, the hemolyzing agent, and the nucleic acid staining reagent is diluted by the diluent, to prepare the first measurement sample. The first measurement sample is used for measuring malaria-infected red blood cells.

The hemolyzing agent stored in the reagent container 51 contains, for example, two kinds of surfactants having different hemolyzing abilities. For example, the hemolyzing agent includes 2.95 mmol/L of lauryl trimethyl ammonium chloride that is a cationic surfactant, and 1.11 mmol/L of stearyl trimethyl ammonium chloride that is a cationic surfactant. Stearyl trimethyl ammonium chloride has a higher hemolyzing ability than lauryl trimethyl ammonium chloride. The two kinds of the surfactants may be another combination of surfactants in a case where the surfactants have different hemolyzing abilities. The hemolyzing agent further includes 2.90 mmol/L of PBC-44 which is a nonionic surfactant, 20 mmol/L of ADA, an appropriate amount of NaCl, and 1 L of purified water. The pH of the ADA is 6.1. The pH of the hemolyzing agent is not less than 5.0 and not greater than 7.0. In order to contract a blood cell, the osmotic pressure of the hemolyzing agent is, for example, not lower than 200 mOsm/kg·$H_2O$ and not higher than 300 mOsm/kg·$H_2O$. Examples of the hemolyzing agent include Lysercell (SYSMEX CORPORATION).

The nucleic acid staining reagent stored in the reagent container 52 contains, for example, a staining dye (Hoechst 34580). The concentration of the staining dye in the nucleic acid staining reagent is, for example, not lower than 0.3 µmol/L and not higher than 0.6 µmol/L, or is 0.45 µmol/L. The concentration of the staining dye in the measurement sample is, for example, not lower than 0.15 µmol/L and not higher than 1.0 µmol/L. The chemical formula of Hoechst 34580 is indicated below.

[Chemical formula 1]

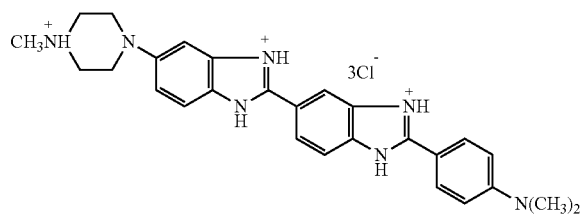

One reagent that contains the staining dye and the hemolyzing agent for contracting a red blood cell may be mixed with a blood sample without separately using the hemolyzing agent and the nucleic acid staining reagent, to prepare the first measurement sample.

Examples of the diluent that is stored in the reagent container 53 and that does not contain a hemolyzing agent and a staining dye include buffer solutions such as CELL-PACK DFL (SYSMEX CORPORATION). The diluent that does not contain a hemolyzing agent is used also as a sheath liquid in measurement of blood cells in a flow cytometry.

The second sample preparation unit 5B has a second reaction chamber 54B and is connected to the reagent container 53.

The suction unit 4 moves the suction tube 20 to a portion above the second reaction chamber 54B and discharges the suctioned blood sample into the second reaction chamber 54B. A diluent is sent from the reagent container 53 into the second reaction chamber 54B. The blood sample and the diluent are mixed in the second reaction chamber 54B, to prepare the second measurement sample. The second measurement sample is used for measuring intrinsic fluorescence of a red blood cell.

Figure 2:
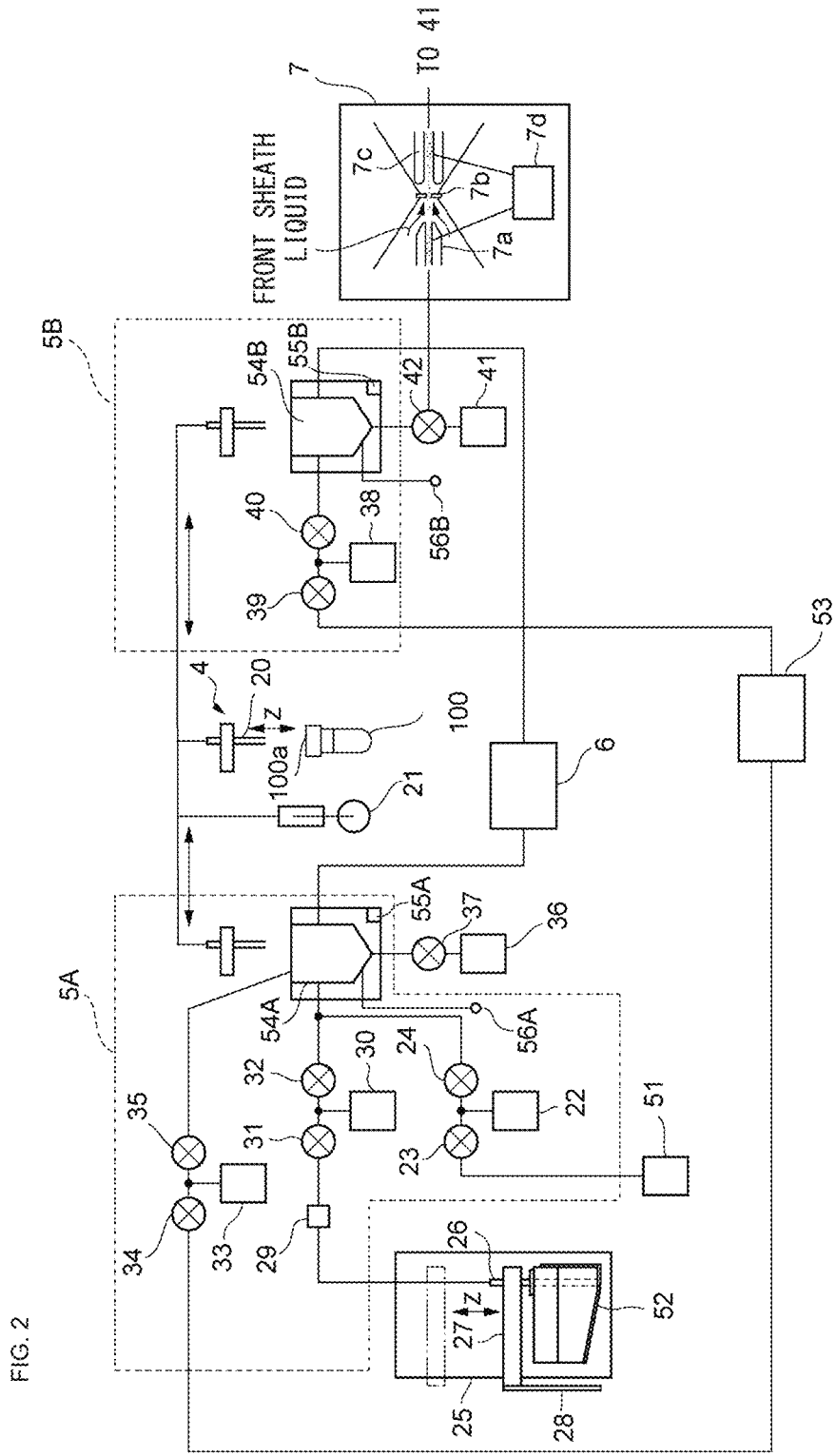
FIG. 2 is a schematic diagram illustrating the configuration of the blood analyzer according to the embodiment.

The configurations of the first sample preparation unit 5A and the second sample preparation unit 5B will be described in more detail. As shown in FIG. 2, the suction unit 4 includes the suction tube 20 in which liquid passes, and the metering unit 21.

The tip of the suction tube 20 can penetrate (puncture) a sealing lid 100a of a sample container 100 that stores a sample. The suction tube 20 can move in the vertical direction (Z direction), and can move to the first reaction chamber 54A and the second reaction chamber 54B. A syringe pump is used for the metering unit 21. Instead of the syringe pump, for example, a diaphragm pump can also be used. The metering unit 21 suctions a predetermined amount of sample from the sample container 100 through the suction tube 20 and discharges the sample. Thus, a predetermined amount of sample necessary for measuring the sample is suctioned from the sample container 100, and the sample can be supplied to the first reaction chamber 54A and the second reaction chamber 54B.

A metering unit 22 and electromagnetic valves 23, 24 are disposed in a flow path between the reagent container 51 that stores the hemolyzing agent, and the first reaction chamber 54A. A syringe pump is used as the metering unit 22. Instead of the syringe pump, for example, a diaphragm pump can also be used. The electromagnetic valves 23, 24 open and close the flow path. The metering unit 22 and the electromagnetic valves 23, 24 quantitatively send the hemolyzing agent in the reagent container 51 to the first reaction chamber 54A.

The reagent container 52 that stores the nucleic acid staining reagent is held by a reagent container holder 25. The reagent container holder 25 has a suction tube 26 for suctioning the nucleic acid staining reagent in the reagent container 52, and a suction tube elevating/lowering mechanism 27 for elevating and lowering the suction tube 26. The tip of the suction tube 26 can penetrate (puncture) a sealing member of the reagent container 52. A cover 28 is connected to the suction tube elevating/lowering mechanism 27. In a state where the suction tube elevating/lowering mechanism 27 is lowered and the suction tube 26 penetrates (punctures) the sealing member of the reagent container 52, the cover 28 is also lowered and covers the reagent container 52. When the suction tube elevating/lowering mechanism 27 is elevated, the cover 28 is also elevated and the reagent container 52 can be removed from outside.

A bubble sensor 29 for detecting bubbles in liquid is disposed in a flow path between the suction tube 26 and the first reaction chamber 54A. A metering unit 30 and electromagnetic valves 31, 32 are disposed in the flow path between the suction tube 26 and the first reaction chamber 54A. A syringe pump is used as the metering unit 30. Instead of the syringe pump, for example, a diaphragm pump can also be used. The electromagnetic valves 31, 32 open and close the flow path. The metering unit 30 and the electromagnetic valves 31, 32 quantitatively send the nucleic acid staining reagent in the reagent container 52 into the first reaction chamber 54A.

A metering unit 33 and electromagnetic valves 34, 35 are disposed in a flow path between the reagent container 53 that stores the diluent, and the first reaction chamber 54A. A syringe pump is used as the metering unit 33. Instead of the syringe pump, for example, a diaphragm pump can also be used.

The electromagnetic valves 34, 35 open and close the flow path. The metering unit 33 and the electromagnetic valves 34, 35 quantitatively send the diluent in the reagent container 53 into the first reaction chamber 54A. A waste liquid chamber 36 for storing unnecessary solution is connected to the first reaction chamber 54A. An electromagnetic valve 37 for opening and closing a flow path is disposed between the first reaction chamber 54A and the waste liquid chamber 36.

A heater 55A for heating liquid in the first reaction chamber 54A is disposed adjacent to the first reaction chamber 54A. The first reaction chamber 54A is connected to a pump 56A for supplying air into the first reaction chamber 54A in order to stir liquid in the first reaction chamber 54A.

A metering unit 38 and electromagnetic valves 39, 40 are disposed in a flow path between the reagent container 53 that stores the diluent, and the second reaction chamber 54B. A syringe pump is used as the metering unit 38. Instead of the syringe pump, for example, a diaphragm pump can also be used. The electromagnetic valves 39, 40 open and close the flow path. The metering unit 38 and the electromagnetic valves 39, 40 quantitatively send the diluent in the reagent container 53 into the second reaction chamber 54B. A waste liquid chamber 41 for storing unnecessary solution is connected to the second reaction chamber 54B. An electromagnetic valve 42 for switching the flow path between a flow path from the second reaction chamber 54B to the waste liquid chamber 41 and a flow path from the second reaction chamber 54B to a second detector unit 7 is disposed between the second reaction chamber 54B and the waste liquid chamber 41.

A heater 55B for heating liquid in the second reaction chamber 54B is disposed adjacent to the second reaction chamber 54B. The second reaction chamber 54B is connected to a pump 56B for supplying air into the second reaction chamber 54B in order to stir liquid in the second reaction chamber 54B.

The measurement unit 2 shown in FIG. 1 further includes an optical detector unit 6 for measuring white blood cells and malaria-infected red blood cells and measuring intrinsic fluorescence of red blood cells, by flow cytometry. The optical detector unit 6 includes a flow cell 61 in which each of the first and the second measurement samples flows, a light source unit 62 for applying light to the first and the second measurement samples flowing in the flow cell 61, and a detection unit 6A for detecting intensities of fluorescence and scattered light which are generated from each of the first and the second measurement samples to which light has been applied. The detection unit 6A includes a detector 63 and a detector 64. The fluorescence includes intrinsic fluorescence.

The first measurement sample prepared by the first sample preparation unit 5A, the second measurement sample prepared by the second sample preparation unit 5B, and the diluent stored in the reagent container 53 are supplied into the flow cell 61. In the flow cell 61, each of the first measurement sample and the second measurement sample is covered by the diluent serving as a sheath liquid.

The light source unit 62 applies, to the flow cell 61, light in a band of wavelength that is not less than 400 nm and not greater than 435 nm. Specifically, the light source unit 62 is a semiconductor laser light source, and applies, to the flow cell 61, blue-violet laser light having a wavelength of 405 nm.

Each of the detectors 63, 64 detects light generated from each of the first measurement sample and the second measurement sample when light is applied to flow of each of the first measurement sample and the second measurement sample in the flow cell 61. A sensitivity wavelength range for each of the detectors 63, 64 is not less than 400 nm and not greater than 1000 nm. The detectors 63, 64 are implemented by avalanche photodiodes. Instead of the avalanche photodiode, another detector such as a laser diode or a photomultiplier can also be used.

In the following description, a direction connecting between the light source unit 62 and the flow cell 61 is referred to as "X direction", and the direction that is orthogonal to the X direction and connects between the flow cell 61 and a mirror 65 is referred to as "Y direction". The detector 63 detects fluorescence generated from each of the first measurement sample and the second measurement sample through the mirror 65 disposed distant from the flow cell 61 in the Y direction. The detector 64 is disposed on the side opposite to the light source unit 62 across the flow cell 61 so as to be distant from the flow cell 61 in the X direction. The detector 64 detects forward scattered light generated from a measurement sample.

A detector may be disposed at an appropriate position relative to the flow cell 61 and detect other scattered light such as side scattered light or backward scattered light instead of forward scattered light.

Each of the detectors 63, 64 outputs an analog signal indicating an intensity of received light. Hereinafter, the analog signal outputted from the detector 63 is referred to as "fluorescence signal", and the analog signal outputted from the detector 64 is referred to as "forward scattered light signal".

The first measurement sample and the second measurement sample may be caused to flow in the flow cell 61 in any order. The first measurement sample may be caused to flow in the flow cell 61 and the second measurement sample may be caused to subsequently flow therein. Alternatively, the second measurement sample may be caused to flow in the flow cell 61 and the first measurement sample may be caused to subsequently flow therein.

The measurement unit 2 further includes a washing unit 8 for washing the flow cell 61, for example, after one of the first and the second measurement samples has passed through the flow cell 61 and before the other of the first and the second measurement samples passes through the flow cell 61. The washing unit 8 includes a metering pump such as a syringe pump or a diaphragm pump, and causes the diluent stored in the reagent container 53 to flow in the flow cell 61, thereby washing the flow cell 61. In a case where the first measurement sample is caused to firstly flow in the flow cell 61, the second measurement sample is caused to flow in the flow cell 61 after the washing unit 8 has washed the flow cell 61. In a case where the second measurement sample is caused to firstly flow in the flow cell 61, the first measurement sample is caused to flow in the flow cell 61 after the washing unit 8 has washed the flow cell 61.

The measurement unit 2 includes the second detector unit 7 for measuring red blood cells by a sheath flow DC detection method. As shown in FIG. 2, the second detector unit 7 is fluidly connected to the second reaction chamber 54B via the electromagnetic valve 42. The second detector unit 7 includes a sample nozzle 7a, an aperture member 7b, a collection tube 7c, and a detector 7d. A measurement sample (third measurement sample) is supplied from the second reaction chamber 54B to the sample nozzle 7a. The measurement sample supplied to the sample nozzle 7a passes through an aperture of the aperture member 7b, collected by the collection tube 7c, and sent to the waste liquid chamber 41. A voltage is applied, by the detector 7d, to the measurement sample that passes through the aperture of the aperture member 7b. When a blood cell passes through a sheath flow cell, the voltage changes due to electric resistance of the blood cell. The detector 7d detects the change of the voltage to detect the electric resistance, thereby detecting the blood cell. The detector 7d outputs an analog signal indicating the voltage. A red blood cell can be detected also by detection of scattered light by the optical detector unit 6. Therefore, the second detector unit 7 may be omitted.

Returning to FIG. 1, the measurement unit 2 further includes a signal processing circuit 81, a microcomputer 82, and a communication interface 83.

The signal processing circuit 81 performs signal processing for analog signals outputted by the detectors 63, 64. The signal processing circuit 81 extracts, as a feature parameter, a peak value of a pulse included in each of the fluorescence signal and the forward scattered light signal. Hereinafter, the peak value of the fluorescence signal is referred to as "fluorescence intensity" and the peak value of the forward scattered light signal is referred to as "forward scattered light intensity".

The microcomputer 82 controls the suction unit 4, the first sample preparation unit 5A, the second sample preparation unit 5B, the optical detector unit 6, the signal processing circuit 81, and the communication interface 83.

The communication interface 83 is connected to the information processing unit 3 via a communication cable. The measurement unit 2 performs data communication with the information processing unit 3 via the communication interface 83. The communication interface 83 transmits the first and the second measurement data including the feature parameters to the information processing unit 3 when the respective first measurement sample and second measurement sample are measured.

The information processing unit 3 generates information about malaria infection, based on an intensity of fluorescence and an intensity of scattered light which are detected from the first measurement sample, and generates information about iron-deficiency anemia, based on an intensity of intrinsic fluorescence of a red blood cell which is detected from the second measurement sample.

Figure 3:
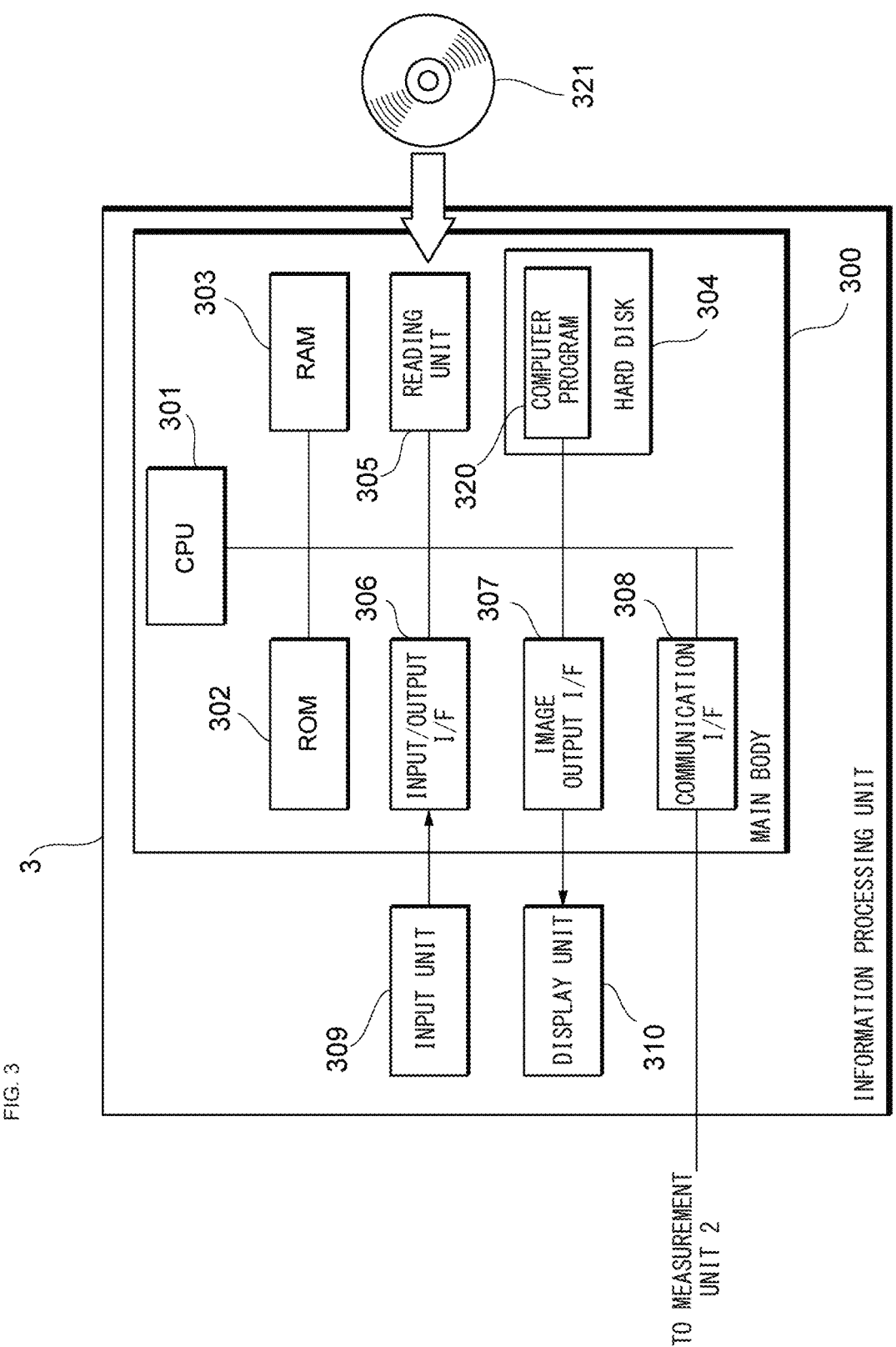
FIG. 3 is a block diagram illustrating a configuration of an information processing unit of the blood analyzer according to the embodiment.

A configuration of the information processing unit 3 will be described with reference to FIG. 3. The information processing unit 3 includes a main body 300, an input unit 309, and a display unit 310. The main body 300 has a CPU (central processing unit) 301, a ROM (read only memory) 302, a RAM (random access memory) 303, a hard disk 304, a reading unit 305, an input/output interface 306, an image output interface 307, and a communication interface 308. The display unit 310 displays characters and images.

The CPU 301 executes a computer program stored in the ROM 302 and executes a computer program loaded into the RAM 303. The RAM 303 is used for reading the computer programs stored in the ROM 302 and the hard disk 304. The RAM 303 is used also as a work area for the CPU 301 when the computer program is executed.

A computer program 320 for analyzing the first and the second measurement data provided by the measurement unit 2 and outputting an analysis result is installed in the hard disk 304.

The reading unit 305 is implemented by a flexible disc drive, a CD-ROM drive, a DVD-ROM drive, or the like, and can read a computer program or data stored in a portable storage medium 321. The computer program 320 for causing a computer to function as the information processing unit 3 is stored in the portable storage medium 321. The computer program 320 read from the portable storage medium 321 is installed in the hard disk 304.

The input unit 309 includes an input device such as a keyboard and a mouse, and is connected to the input/output interface 306. The display unit 310 is connected to the image output interface 307. The communication interface 308 is connected to the communication interface 83 of the measurement unit 2.

<Operation of Blood Analyzer>

An operation of the blood analyzer 1 will be described with reference to FIG. 4.

Firstly, the CPU 301 of the information processing unit 3 receives an instruction for performing measurement, from a user, via the input unit 309 (step S101). Upon receiving the instruction for performing the measurement, the CPU 301 operates to transmit, to the measurement unit 2, instruction data of an instruction for starting the measurement (step S102), and the measurement unit 2 receives the instruction data (step S103). The microcomputer 82 performs a first measurement sample preparation process (step S104), a first measurement process (step S105), a second measurement sample preparation process (step S106), and a second measurement process (step S107). The second measurement sample preparation process (step S106) and the second measurement process (step S107) may be performed before the first measurement sample preparation process (step S104) and first measurement process (step S105).

Figure 5:
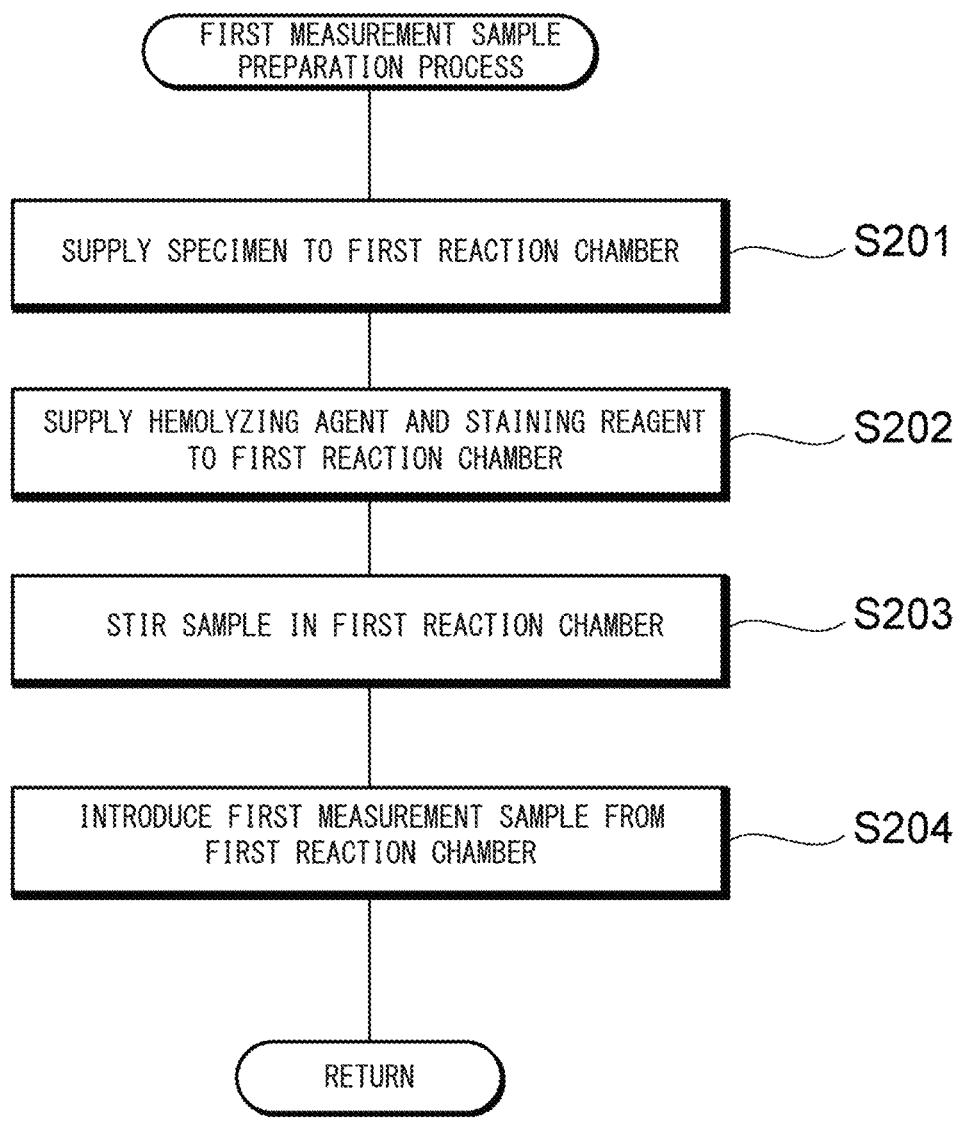
FIG. 5 is a flow chart showing a procedure of a first measurement sample preparation process according to the embodiment.

The first measurement sample preparation process (step S104) will be described with reference to FIG. 5. The microcomputer 82 performs control such that the suction unit 4 supplies a predetermined amount, for example, 17 μL of blood sample to the first reaction chamber 54A (step S201). Subsequently, the microcomputer 82 performs control such that the first sample preparation unit 5A supplies a predetermined amount, for example, 1 mL of the hemolyzing agent from the reagent container 51 to the first reaction chamber 54A, and supplies a predetermined amount, for example, 20 μL of the nucleic acid staining reagent from the reagent container 52 to the first reaction chamber 54A (step S202).

The first reaction chamber 54A is heated to a predetermined temperature by the heater 55A. In the heated state, the mixture in the first reaction chamber 54A is stirred by using the pump 56A (step S203). The blood sample, the hemolyzing agent, and the nucleic acid staining reagent are caused to react with each other, and the microcomputer 82 thereafter performs control such that the first sample preparation unit 5A supplies a predetermined amount of the diluent from the reagent container 53 to the first reaction chamber 54A, to dilute the reaction solution of the blood sample, the hemolyzing agent, and the nucleic acid staining reagent, thereby preparing the first measurement sample. Subsequently, the microcomputer 82 performs control such that the first sample preparation unit 5A introduces the first measurement sample from the first reaction chamber 54A to the optical detector unit 6 (step S204).

When the process step in step S204 has ended, the microcomputer 82 returns the process to a main routine.

FIG. 4 is referred to again. In the first measurement process (step S105), the optical detector unit 6 measures the first measurement sample. The first sample preparation unit 5A supplies both the sheath liquid and the first measurement sample to the flow cell 61. The light source unit 62 applies light to flow of the first measurement sample in the flow cell 61.

The first measurement sample flows in the flow cell 61, and blood cells including white blood cells, aggregate platelets, and red blood cells sequentially pass through the flow cell 61. In the description herein, the "aggregate platelets" refer to an aggregate of two or more platelets. In a case where a red blood cell infected with malaria (hereinafter, referred to as "malaria-infected red blood cell") is included, *Plasmodium* is in the malaria-infected red blood cell. The red blood cell in the measurement sample is contracted by the action of the hemolyzing agent. The malaria-infected red blood cell is contracted by the hemolyzing agent while having *Plasmodium* therein. Furthermore, *Plasmodium* has a nucleus, and the nucleus is stained by the nucleic acid staining reagent. The white blood cell also has a nucleus, and is thus stained by the staining reagent. Neither red blood cells (hereinafter, referred to as "normal red blood cell") which are not infected with *Plasmodium* nor aggregate platelets have nuclei, and are hardly stained by the nucleic acid staining reagent.

Each time light is applied to the blood cell (white blood cell, aggregate platelets, and red blood cell), scattered light is generated from the blood cell, and fluorescence is generated according to a kind of the blood cell. The detector 63 detects the fluorescence generated from the blood cell. The detector 64 detects the scattered light (forward scattered light) generated from the blood cell.

Each of the detectors 63, 64 outputs an electric signal based on the level of the received light, as the fluorescence signal and the forward scattered light signal. The signal processing circuit 81 extracts the fluorescence intensity from the fluorescence signal and extracts the forward scattered light intensity from the forward scattered light signal. After the first measurement sample has flowed through the flow cell 61, the washing unit 8 washes the flow cell 61.

Figure 6:
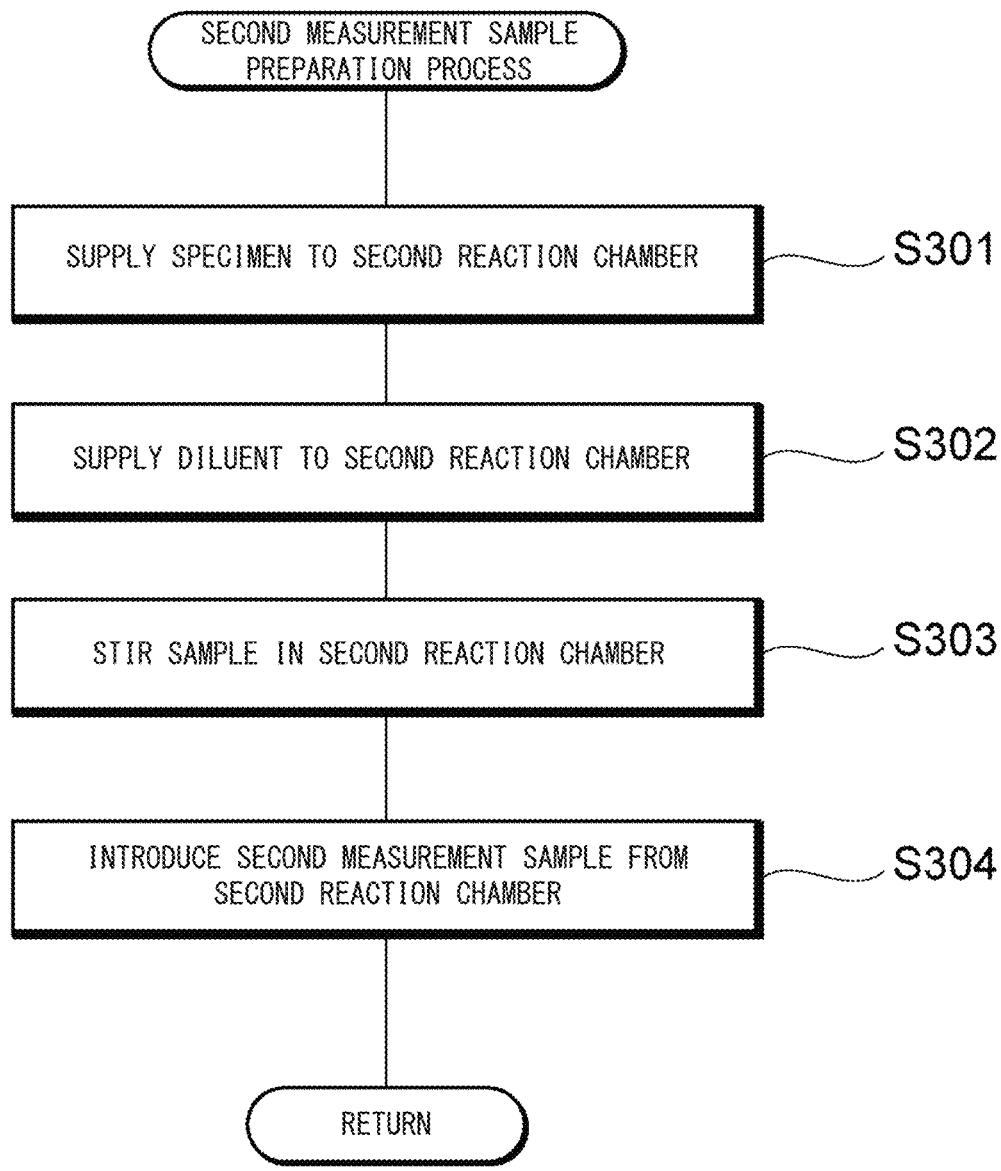
FIG. 6 is a flow chart showing a procedure of a second measurement sample preparation process according to the embodiment.

The second measurement sample preparation process (step S106) will be described. In FIG. 6, in step S301, the microcomputer 82 performs control such that the suction unit 4 suctions a predetermined amount of blood sample from a test tube, and supplies 5 μL of the sample to the second reaction chamber 54B. Subsequently, in step S302, the microcomputer 82 performs control such that the second sample preparation unit 5B supplies 1020 μL of the diluent from the reagent container 53 to the second reaction chamber 54B.

The second reaction chamber 54B is heated to a predetermined temperature by the heater 55B. In the heated state, the mixture in the second reaction chamber 54B is stirred by using the pump 56B in step S303. In the operations from step S301 to S303, the second measurement sample is prepared in the second reaction chamber 54B. In the second measurement sample, the blood cells are not hemolyzed and stained. In step S304, the microcomputer 82 performs control such that the second sample preparation unit 5B introduces the second measurement sample from the second reaction chamber 54B to the optical detector unit 6.

When the process step of step S304 has ended, the microcomputer 82 returns the process to the main routine.

FIG. 4 is referred to again. In the second measurement process (step S107), the optical detector unit 6 measures the second measurement sample. Both the sheath liquid and the second measurement sample are supplied to the flow cell 61. The light source unit 62 applies light to flow of the second measurement sample in the flow cell 61.

The second measurement sample flows in the flow cell 61, and blood cells including red blood cells sequentially pass through the flow cell 61. An amount of protoporphyrin in red blood cells of a healthy person is small, whereas a large amount of protoporphyrin is contained in red blood cells of an iron-deficiency anemia patient. In a case where blue-violet laser light is applied to red blood cells containing a large amount of protoporphyrin, intrinsic fluorescence is generated. The intrinsic fluorescence is red light having a wavelength of not less than 600 nm and not greater than 700 nm, and the intrinsic fluorescence generated from each of the red blood cells is individually detected by the detector 63. Meanwhile, if blue laser light is applied to red blood cells in which an amount of protoporphyrin is small, intrinsic fluorescence is hardly generated. Therefore, the level of the received light by the detector 63 indicates a small value, and intrinsic fluorescence is not detected.

Each time light is applied to the red blood cell, scattered light is generated from the red blood cell. The scattered light (forward scattered light) generated from the red blood cell has a wavelength of 405 nm and is detected by the detector 64.

The detector 63 and the detector 64 each output an electric signal based on the level of the received light, as the fluorescence signal and the forward scattered light signal. The signal processing circuit 81 extracts the fluorescence intensity from the fluorescence signal, and extracts the forward scattered light intensity from the forward scattered light signal. After the second measurement sample has flowed through the flow cell 61, the washing unit 8 washes the flow cell 61.

In a third measurement sample preparation process (step S108), the microcomputer 82 performs control such that the suction unit 4 suctions a predetermined amount of blood sample from a test tube, and supplies 5 μL of the sample to the second reaction chamber 54B. Subsequently, the microcomputer 82 performs control such that the second sample preparation unit 5B supplies 1020 μL of the diluent from the reagent container 53 to the second reaction chamber 54B, thereby preparing the third measurement sample.

In a third measurement process (step S109), the second detector unit 7 measures the third measurement sample. The second detector unit 7 applies a voltage to the third measurement sample flowing in the sheath flow cell, and outputs an analog signal indicating the voltage, to the signal processing circuit 81. Each time a red blood cell passes through the sheath flow cell, the voltage changes according to electric resistance. The signal processing circuit 81 detects the change of the electric resistance by signal processing and detects the red blood cell. Thus, the signal processing circuit 81 converts the output signal from the second detector unit 7, to detection data of the red blood cell. After the third measurement process, the microcomputer 82 operates to transmit first, second, and third measurement data including feature parameters to the information processing unit 3 (step S110), and ends the process.

The information processing unit 3 receives the first, the second, and the third measurement data (step S111). Subsequently, the CPU 301 analyzes the detection data of the red blood cells included in the third measurement data, and counts the red blood cells (step S112). Thereafter, the CPU 301 performs a first measurement data analysis process for generating information about malaria infection, and generates an analysis result of the blood sample, and stores the analysis result in the hard disk 304 (step S113).

Figure 7:
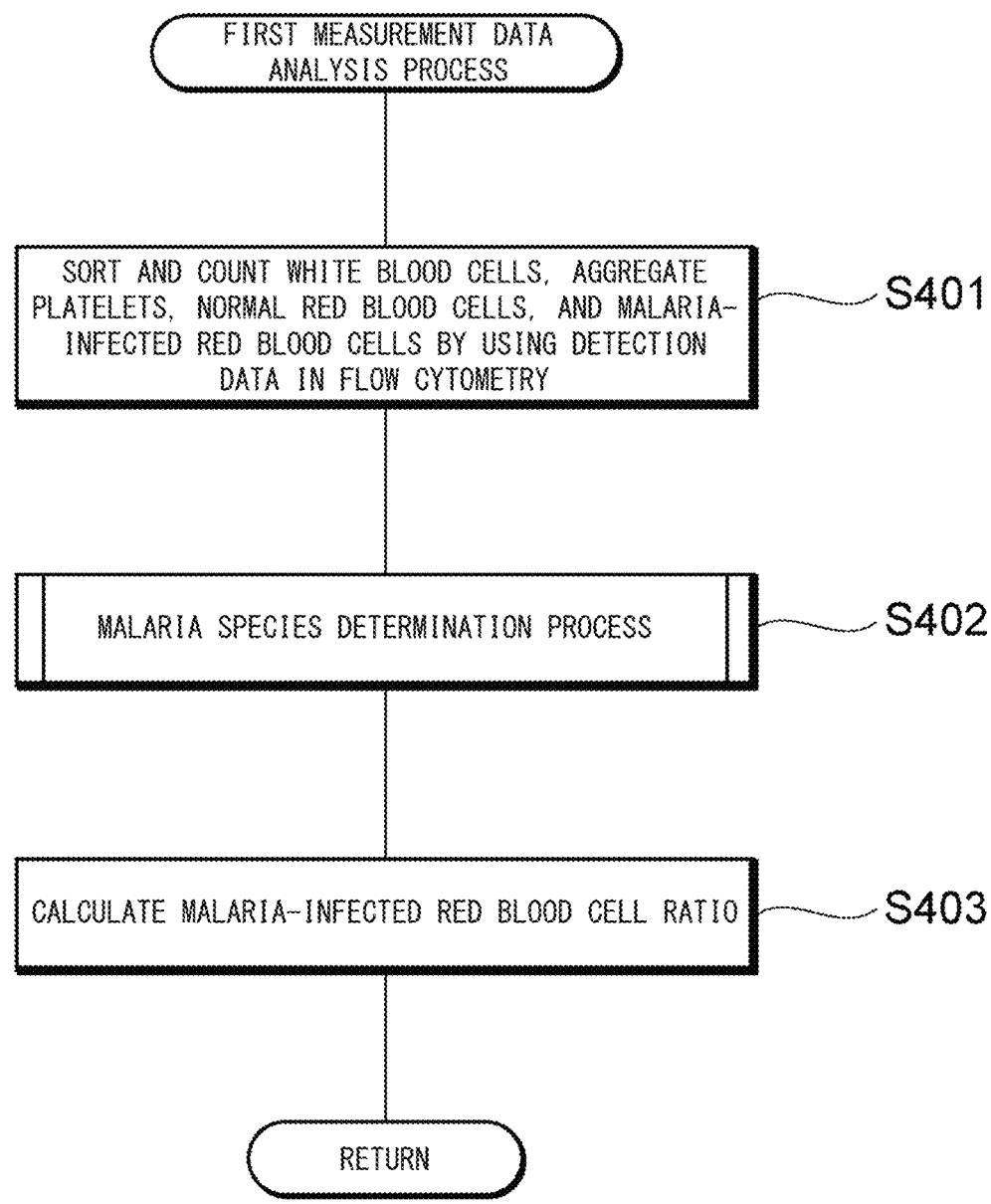
FIG. 7 is a flow chart showing a procedure of a first measurement data analysis process according to the embodiment.

The first measurement data analysis process will be described with reference to FIG. 7. When the first measurement data analysis process starts, the CPU 301 firstly sorts the detected blood cells into white blood cells, aggregate platelets, normal red blood cells, and malaria-infected red blood cells based on the fluorescence intensity and the forward scattered light intensity included in the first measurement data, and counts each of the white blood cells, the aggregate platelets, the normal red blood cells, and the malaria-infected red blood cells (step S401).

Figure 8:
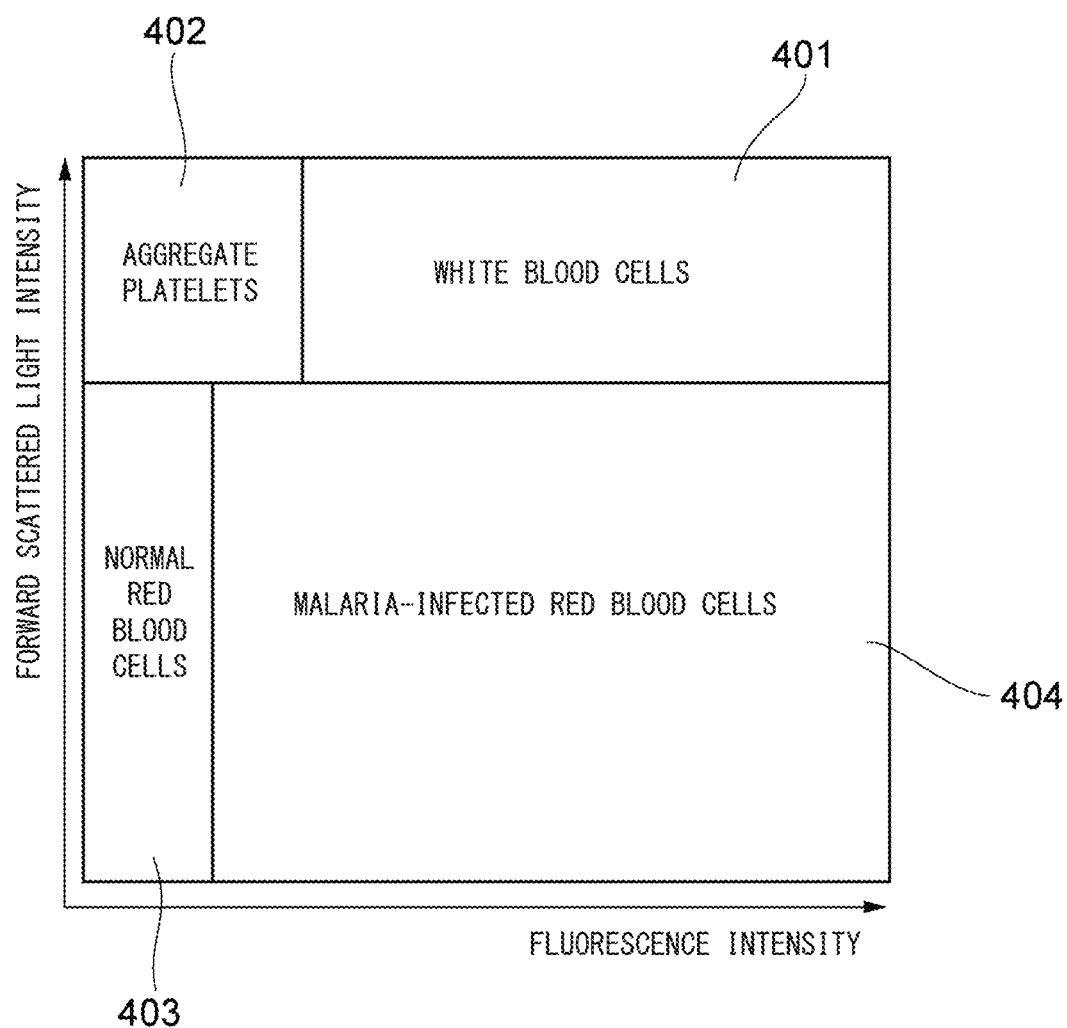
FIG. 8 is a schematic diagram illustrating regions in which particle groups of white blood cells, aggregate platelets, normal red blood cells, and malaria-infected red blood cells appear, in a scattergram in which the vertical axis represents forward scattered light intensities and the horizontal axis represents fluorescence intensities, according to the embodiment.

An operation of sorting the detected blood cells into white blood cells, aggregate platelets, normal red blood cells, and malaria-infected red blood cells will be described with reference to FIG. 8. In the scattergram illustrated in FIG. 8, the vertical axis represents forward scattered light intensities, and the horizontal axis represents fluorescence intensities.

The white blood cells substantially appear in a region 401 (hereinafter, a particle group in the region 401 is referred to as a first particle group) in which the forward scattered light intensity is higher than that of an aggregation of normal red blood cells and malaria-infected red blood cells, and the fluorescence intensity is higher than that of an aggregation of the normal red blood cells and aggregate platelets. The aggregate platelets substantially appear in a region 402 in which the forward scattered light intensity is almost the same as that in the region 401, and the fluorescence intensity is lower than that in the region 401. The normal red blood cell is highly contracted by the hemolyzing agent. Therefore, the normal red blood cells contracted by the hemolyzing agent substantially appear in a region 403 (hereinafter, a particle group in the region 403 is referred to as a second particle group) in which the forward scattered light intensity is lower than that in the region 401, and the fluorescence intensity is lower than that in the region 401.

The malaria-infected red blood cells are contracted by the hemolyzing agent and each contains *Plasmodium* having a nucleus therein, and is thus stained by the nucleic acid staining reagent. Therefore, the malaria-infected red blood cells substantially appear in a region 404 (hereinafter, a particle group in the region 404 is referred to as a third particle group) in which the forward scattered light intensity is lower than that in the region 401 and the fluorescence intensity is higher than that in the region 403.

Figure 10:
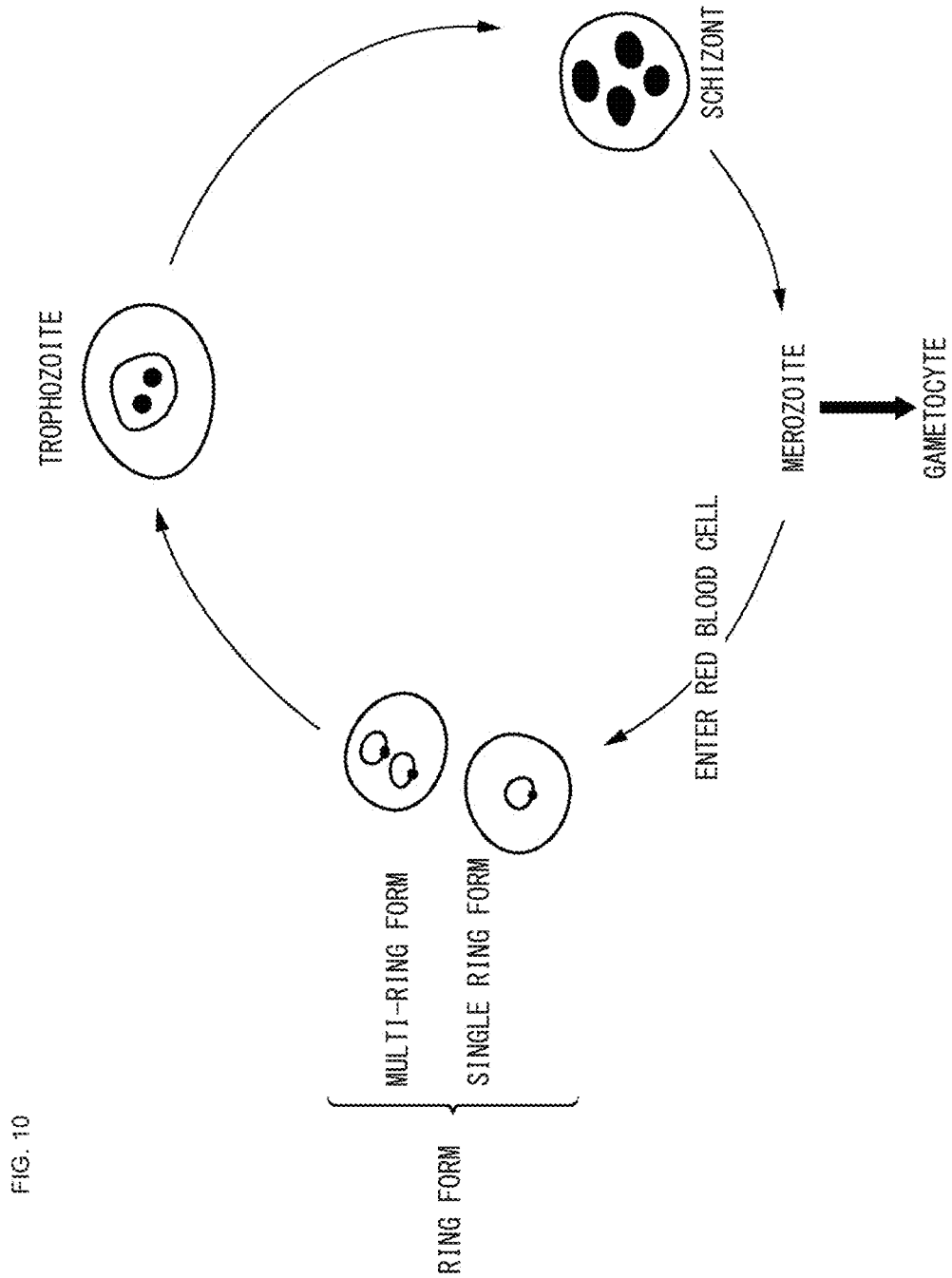
FIG. 10 illustrates a life cycle of *Plasmodium*.
Figure 11:
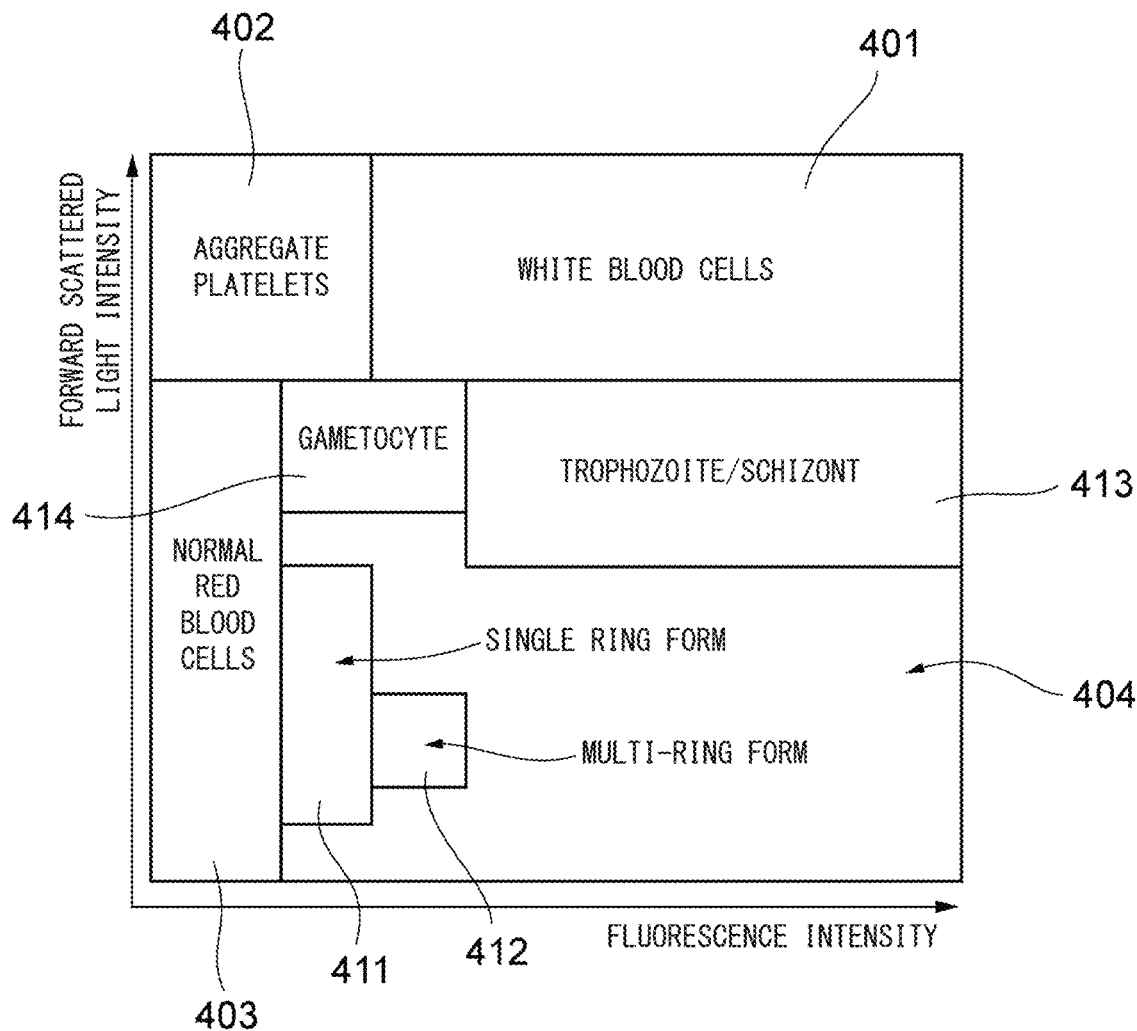
FIG. 11 is a schematic diagram illustrating regions in which particle groups of white blood cells, aggregate platelets, normal red blood cells, single ring forms, multi-ring forms, trophozoites/schizonts, and gametocytes appear, in a scattergram in which the vertical axis represents forward scattered light intensities and the horizontal axis represents fluorescence intensities, according to the embodiment.

Sorting the malaria-infected red blood cells into sub-aggregations will be described with reference to FIG. 10 and FIG. 11. As illustrated in FIG. 10, if blood is sucked by an anopheline having *Plasmodium*, both saliva and a protozoan of the anopheline are injected into blood. The protozoan enters a hepatic cell and proliferates in the cell, and is released again into the blood. At this time, the morphology of the protozoan is called merozoite. If the merozoite is released into the blood, the merozoite immediately enters a red blood cell, and grows while changing the morphology. This morphology change is called a life cycle, and stages in the life cycle are called ring form, trophozoite, and schizont. The ring form includes a single ring form in which one ring form is included in a red blood cell and a multi-ring form in which a plurality of ring forms are included in a red blood cell. The protozoan that has grown to a schizont destroys the red blood cell, becomes a merozoite again, and is released into the blood. The released merozoite enters a red blood cell, and repeats the life cycle and proliferation again. *Plasmodium* proliferates by repeating such a cycle, and continues to destroy red blood cells in the blood. A part of the merozoites is differentiated into a morphology called gametocyte without infecting red blood cells. The gametocyte becomes a matrix for further infection by the blood being sucked by an anopheline. The single ring form, multi-ring form, trophozoite, schizont, and gametocyte have the respective sizes and staining degrees different from each other, and can be classified in a scattergram illustrated in FIG. 11 in which the vertical axis represents forward scattered light intensities, and the horizontal axis represents fluorescence intensities. The trophozoite or schizont appears in a region 413 in which the fluorescence intensity and the forward scattered light intensity are higher than those of the ring form in a region 404 in which malaria-infected red blood cells appear. The gametocyte appears in a region 414 in which the fluorescence intensity is lower than that of the trophozoite or schizont, and the forward scattered light intensity is about the same as that of the trophozoite or schizont which has a higher forward scattered light intensity. The single ring form appears in a region 411 in which the fluorescence intensity is about the same as that of the gametocyte having a lower fluorescence intensity, and the forward scattered light intensity is lower than that of the gametocyte. The multi-ring form appears in a region 412 in which the fluorescence intensity is higher than that of the single ring form, and the forward scattered light intensity is about the same as that of the single ring form having a lower forward scattered light intensity.

Returning to FIG. 7, the CPU 301 performs a malaria species determination process in step S402.

Figure 9:
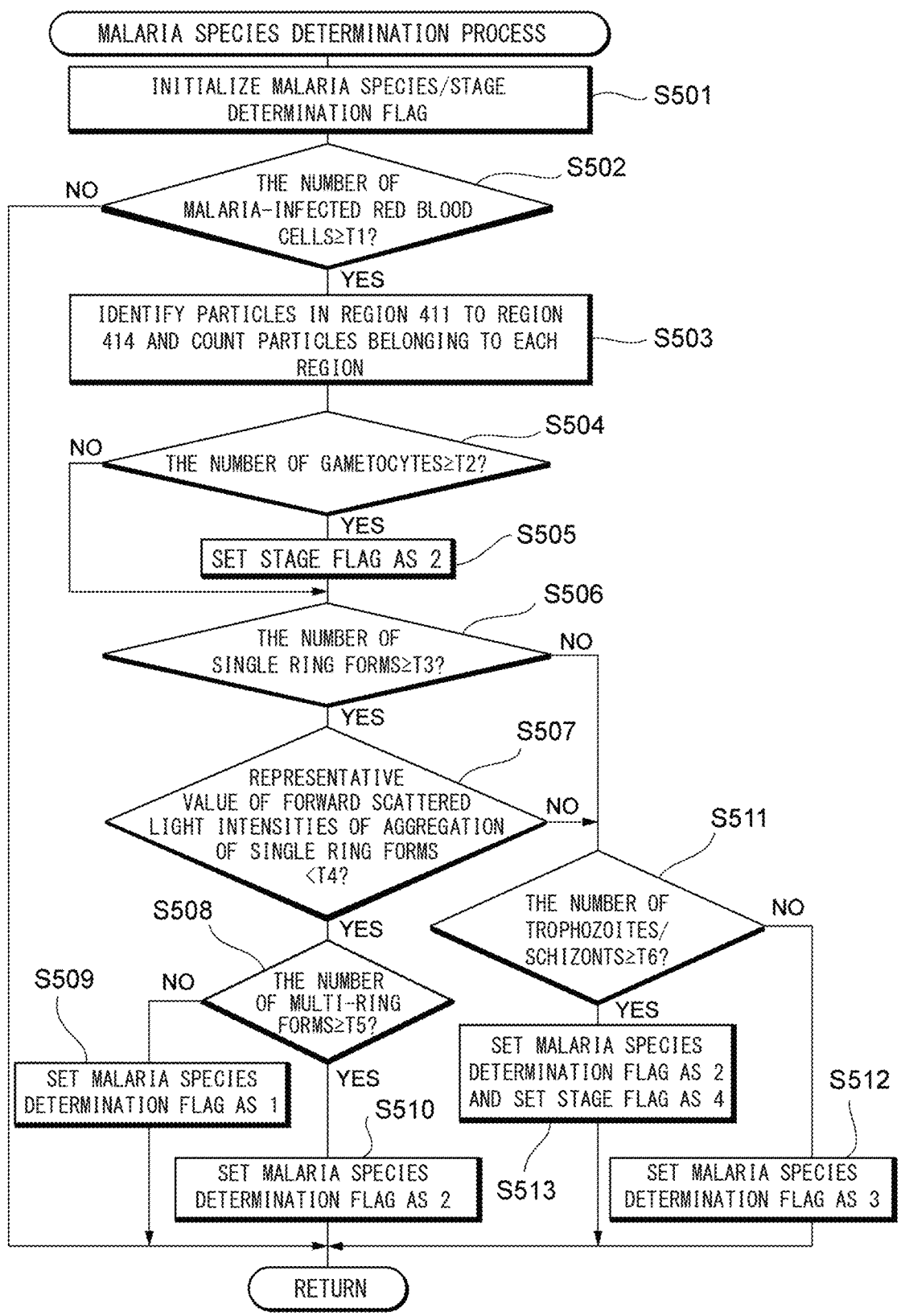
FIG. 9 is a flow chart showing a procedure of a malaria species determination process according to the embodiment.

The malaria species determination process will be described with reference to FIG. 9. The malaria species determination process is a process for determining whether a blood sample is suspected of being infected with *Plasmodium falciparum*, or with another species of *Plasmodium* (hereinafter, referred to "the other species") other than falciparum malaria. The falciparum malaria is a febris that is also called as malignant malaria, and enhances mortality. Therefore, distinguishing falciparum malaria from the other species has high clinical significance. It is known that ring forms are more likely to appear in falciparum malaria than in the species other than falciparum malaria.

In step S501, the CPU 301 sets a malaria species/stage determination flag as 0. The malaria species/stage determination flag is located in a specific region in the RAM 303. The malaria species/stage determination flag having been set as 0 indicates that the blood sample is less likely to be infected with *Plasmodium*. The malaria species/stage determination flag having been set as 1 indicates that the blood sample is suspected of being infected with *Plasmodium falciparum*. The malaria species/stage determination flag having been set as 2 indicates that the blood sample is highly likely to be infected with *Plasmodium falciparum*. That the blood sample is suspected of being infected with *Plasmodium falciparum* means that the blood sample is likely to be infected with *Plasmodium falciparum* but is not highly likely to be infected therewith. Both of the malaria species/stage determination flags having been set as 2 and 3 mean that infection with *Plasmodium falciparum* is likely to occur. The malaria species/stage determination flag having been set as 3 indicates that the blood sample is suspected of being infected with the other species of *Plasmodium*. The malaria species/stage determination flag having been set as 4 indicates that the blood sample is highly likely to be infected with the other species of *Plasmodium*. That the blood sample is suspected of being infected with the other species of *Plasmodium* means that the blood sample is likely to be infected with the other species of *Plasmodium* but is not highly likely to be infected therewith. Both of the malaria species/stage determination flags having been set as 3 and 4 mean that infection with the other species of *Plasmodium* is likely to occur.

In step S502, the CPU 301 determines whether or not the number of malaria-infected red blood cells counted in step S401 is not less than a threshold value T1. In the description herein, the threshold value T1 is set such that, in a case where the number of malaria-infected red blood cells is less than T1, it can be determined that malaria-infected red blood cells do not appear. In a case where the number of malaria-infected red blood cells is less than T1 (NO in step S502), the blood sample can be determined as being not infected with *Plasmodium*. In this case, the CPU 301 ends the malaria species determination process, and the process proceeds to calculation of a malaria-infected red blood cell ratio (step S403).

In a case where a result of comparison between the number of the malaria-infected red blood cells and the threshold value T1 indicates that the number of malaria-infected red blood cells is not less than T1 (YES in step S502), the blood sample can be determined as being likely to be infected with *Plasmodium*. In this case, the CPU 301 shifts the process to step S503.

In step S503, the CPU 301 counts particles belonging to the region 411 in the scattergram illustrated in FIG. 11, as single ring forms, counts particles belonging to the region 412, as multi-ring forms, counts particles belonging to the region 413, as trophozoites or schizonts (hereinafter, referred to as "trophozoites/schizonts"), and counts particles belonging to the region 414, as gametocytes (step S503).

In step S504, the CPU 301 determines whether or not the number of gametocytes is not less than a threshold value T2. The threshold value T2 is set such that, in a case where the number of gametocytes is less than T2, it can be determined that gametocytes do not appear. In a case where the number of gametocytes is not less than T2 (YES in step S504), the gametocytes can be determined as appearing in the blood sample. In this case, the CPU 301 sets the stage flag as 2 (step S505) and shifts the process to step S506.

In a case where the number of the gametocytes is less than T2 (NO in step S504), it can be determined that gametocytes do not appear in the blood sample. In this case, the CPU 301 shifts the process to step S506.

In step S506, the CPU 301 determines whether or not the number of single ring forms is not less than a threshold value T3 (step S506). The threshold value T3 is set such that, in a case where the number of single ring forms is less than T3, it can be determined that single ring forms do not appear. In a case where the number of the single ring forms is less than T3 (NO in step S506), the CPU 301 shifts the process to step S511.

In a case where the number of the single ring forms is not less than T3 (YES in step S506), the CPU 301 determines whether or not a representative value of the forward scattered light intensities is not less than a threshold value T4 in the region 411 in which the single ring forms appear (step S507).

The size of the single ring form of *Plasmodium falciparum* is smaller than the size of the single ring form of the other species of *Plasmodium*. The forward scattered light intensity represents the size of a cell. The representative value of the forward scattered light intensities in the region 411 in which the single ring forms appear is an average value of the forward scattered light intensities of a plurality of particles that appear in the region 411. The threshold value T4 is set such that, in a case where the representative value is less than T4, it can be determined that falciparum malaria infection is likely to occur.

In a case where the representative value of the forward scattered light intensities in the region 411 is less than T4 (YES in step S507), *Plasmodium falciparum* infection is likely to occur. In this case, the CPU 301 determines whether or not the number of multi-ring forms is not less than a threshold value T5 (step S508). The threshold value T5 is set such that, in a case where the number of the multi-ring forms is less than T5, it can be determined that multi-ring forms do not appear.

In a case where the number of the multi-ring forms is less than T5 (NO in step S508), it can be determined that multi-ring forms do not appear in the blood sample. In this case, the blood sample cannot be determined as being highly likely to be infected with *Plasmodium falciparum*. However, in step S507, the blood sample is determined as being likely to be infected with *Plasmodium falciparum*. Therefore, the CPU 301 sets the malaria species determination flag as 1 (step S509), ends the malaria species determination process, and returns the process to the first measurement data analysis process.

In a case where the number of multi-ring forms is not less than T5 (YES in step S508), multi-ring forms can be determined as being likely to appear in the blood sample. In this case, the blood sample can be determined as being highly likely to be infected with *Plasmodium falciparum*. Therefore, the CPU 301 sets the malaria species determination flag as 2 (step S510), ends the malaria species determination process, and returns the process to the first measurement data analysis process.

In a case where the representative value of the forward scattered light intensities is not less than T4 in the region 411 in which single ring forms appear (NO in step S507), infection with the other species of *Plasmodium* is likely to occur. In this case, the CPU 301 determines whether or not the number of trophozoites/schizonts is not less than a threshold value T6 (step S511). The threshold value T6 is set such that, in a case where the number of trophozoites/schizonts is less than T6, it can be determined that trophozoites/schizonts do not appear in the blood sample.

The number of trophozoites/schizonts appearing in peripheral blood of a person infected with *Plasmodium falciparum* is small, and trophozoites/schizonts often appear in peripheral blood of a person infected with the other species of *Plasmodium*. In a case where the number of trophozoites/schizonts is less than T6 (NO in step S511), it can be determined that trophozoites/schizonts do not appear in the blood sample. In this case, the blood sample cannot be determined as being highly likely to be infected with the other species of *Plasmodium*. However, in step S507, the blood sample is determined to be suspected of being infected with the other species of *Plasmodium*. Therefore, the CPU 301 sets the malaria species/stage determination flag as 3 (step S512), ends the malaria species determination process, and returns the process to the first measurement data analysis process.

In a case where the number of trophozoites/schizonts is not less than T6 (YES in step S511), trophozoites/schizonts can be determined as appearing in the blood sample. Furthermore, in this case, the blood sample can be determined as being highly likely to be infected with the other species of *Plasmodium*. Therefore, the CPU 301 sets the malaria species/stage determination flag as 4 (step S513), ends the malaria species determination process, and returns the process to the first measurement data analysis process.

Figure 12:
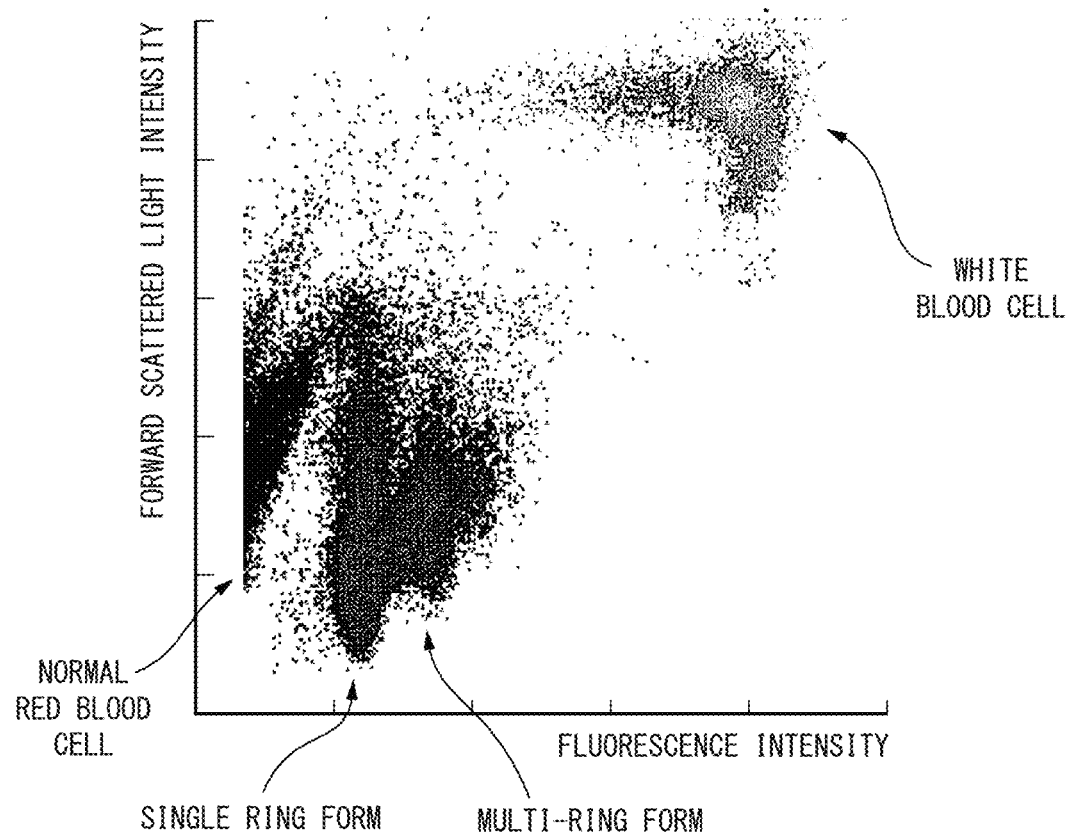
FIG. 12 illustrates an example of a scattergram of a blood sample infected with *Plasmodium*.
Figure 13:
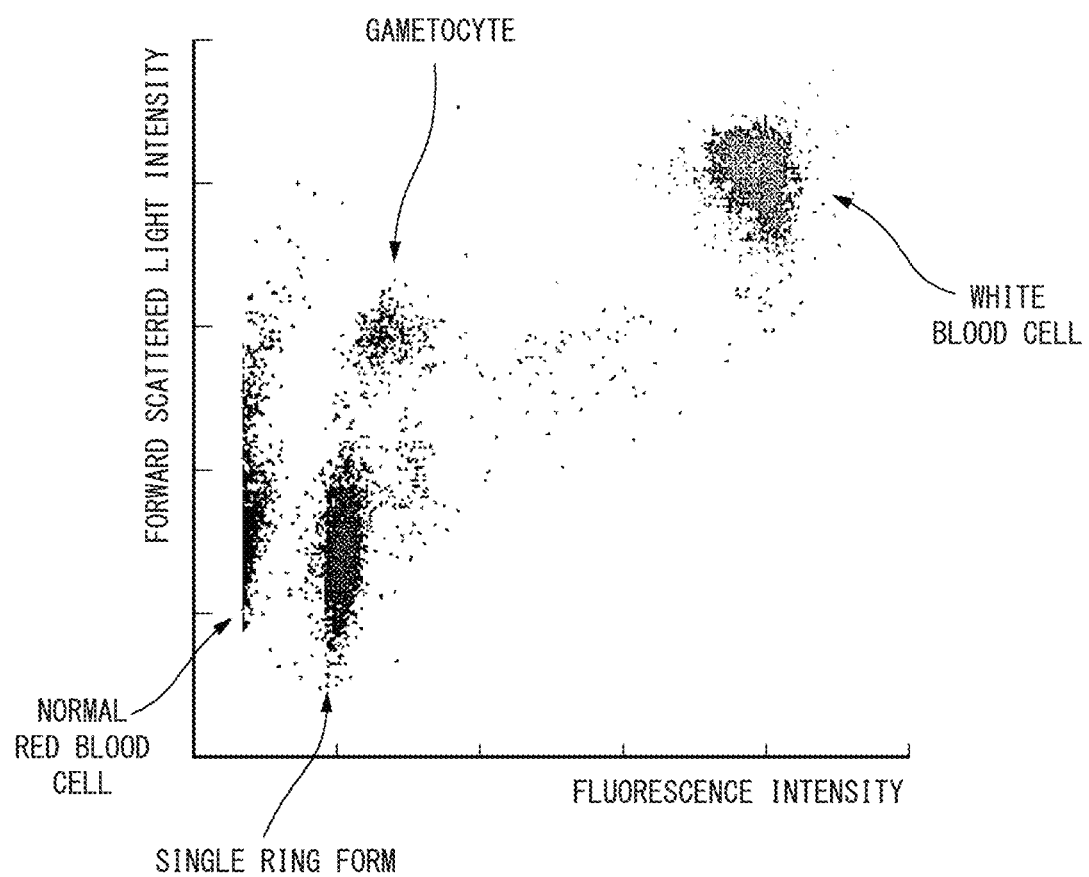
FIG. 13 illustrates an example of a scattergram of a blood sample infected with *Plasmodium*.
Figure 14:
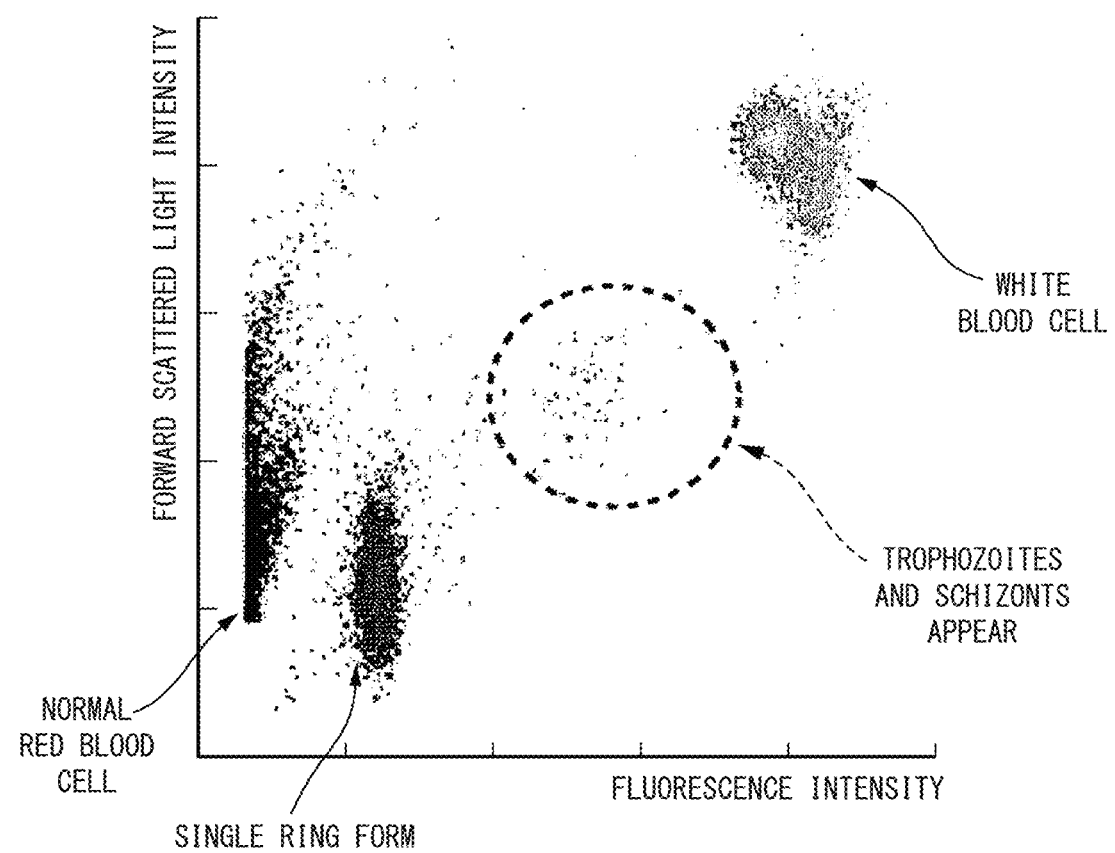
FIG. 14 illustrates an example of a scattergram of a blood sample infected with *Plasmodium*.

An example of a scattergram in the malaria species determination by the blood analyzer according to the present embodiment will be described. FIG. 12 illustrates an example of a scattergram in which an aggregation of single ring forms and an aggregation of multi-ring forms appear. As illustrated in FIG. 12, the forward scattered light intensity and the fluorescence intensity of the aggregation of single ring forms are lower than those of the aggregation of white blood cells. Furthermore, the fluorescence intensity of the aggregation of single ring forms is lower than that of the aggregation of multi-ring forms. FIG. 13 illustrates an example of a scattergram in which an aggregation of single ring forms and an aggregation of gametocytes appear. As illustrated in FIG. 13, the forward scattered light intensity of the aggregation of gametocytes is higher than that of the aggregation of single ring forms, and the fluorescence intensity thereof is about the same as or higher than that of the aggregation of single ring forms. FIG. 14 illustrates an example of a scattergram in which an aggregation of single ring forms and an aggregation of trophozoites/schizonts appear. As illustrated in FIG. 14, the fluorescence intensity of the aggregation of trophozoites/schizonts is higher than that of the aggregation of single ring forms.

FIG. 7 is referred to again. The malaria species determination process as described above ends, and the CPU 301 then calculates a ratio (hereinafter, referred to as "malaria-infected red blood cell ratio") of the number of malaria-infected red blood cells (the number of blood cells in the region 404) to the total number of red blood cells (the number of red blood cells counted in step S112) (step S403). The CPU 301 then ends the first measurement data analysis process, and returns the process to the main routine shown in FIG. 4.

Next, the CPU 301 performs a second measurement data analysis process for generating information about iron-deficiency anemia, generates a result of analysis of the blood sample, and stores the analysis result in the hard disk 304 (step S114). The CPU 301 may firstly perform the second measurement data analysis process (step S114) and subsequently perform the first measurement data analysis process (step S113).

Figure 15:
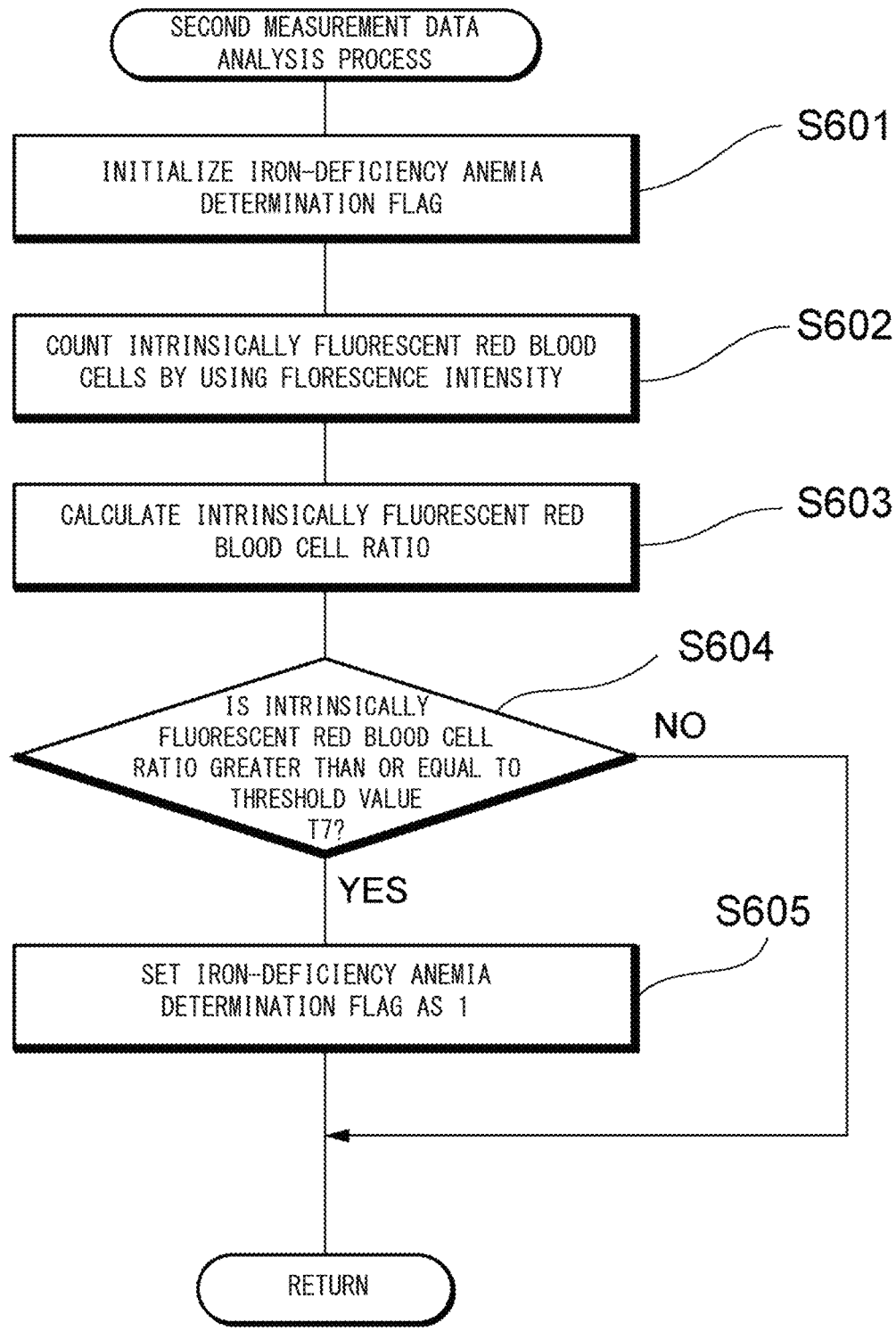
FIG. 15 is a flow chart showing a procedure of a second measurement data analysis process according to the embodiment.

The second measurement data analysis process will be described with reference to FIG. 15. The second measurement data analysis process starts, and, then, the CPU 301 firstly sets, as 0, an initial value of an iron-deficiency anemia determination flag representing possibility of iron-deficiency anemia in step S601. The iron-deficiency anemia determination flag is stored in a specific region of the RAM 303. The iron-deficiency anemia determination flag having been set as 0 indicates that iron-deficiency anemia is less likely to occur, and the iron-deficiency anemia determination flag having been set as 1 indicates that iron-deficiency anemia is likely to occur.

In step S602, the CPU 301 extracts particles in which the fluorescence intensity is not less than a predetermined threshold value, as red blood cells (hereinafter, referred to as "intrinsically fluorescent red blood cell") that generate intrinsic fluorescence, from an aggregation of particles determined as red blood cells, and counts the intrinsically fluorescent red blood cells. Hereinafter, the number of the intrinsically fluorescent red blood cells is referred to as "intrinsically fluorescent red blood cell number". A red blood cell in which the fluorescence intensity having the threshold value or a greater value is not detected is referred to as "red blood cell that does not generate intrinsic fluorescence".

The process step of step S602 will be described with reference to FIG. 16A to FIG. 16D. The CPU 301 generates a scattergram 4000, for a group of particles in the region 403 in the scattergram generated in step S401 shown in FIG. 7, in which the vertical axis represents forward scattered light intensities, and the horizontal axis represents fluorescence intensities. The CPU 301 identifies, as red blood cells that do not generate intrinsic fluorescence, particles in a region 400 in which the forward scattered light intensity is higher than that in a noise region 490, and the fluorescence intensity is lower than that in a region 410 in which intrinsically fluorescent red blood cells appear. The CPU 301 identifies, as intrinsically fluorescent red blood cells, particles in the region 410 in which the forward scattered light intensity is about the same as that in the region 400, and the fluorescence intensity is higher than that in the region 400. The CPU 301 counts the particles in the region 410, and determines the intrinsically fluorescent red blood cell number.

Figure 16A:
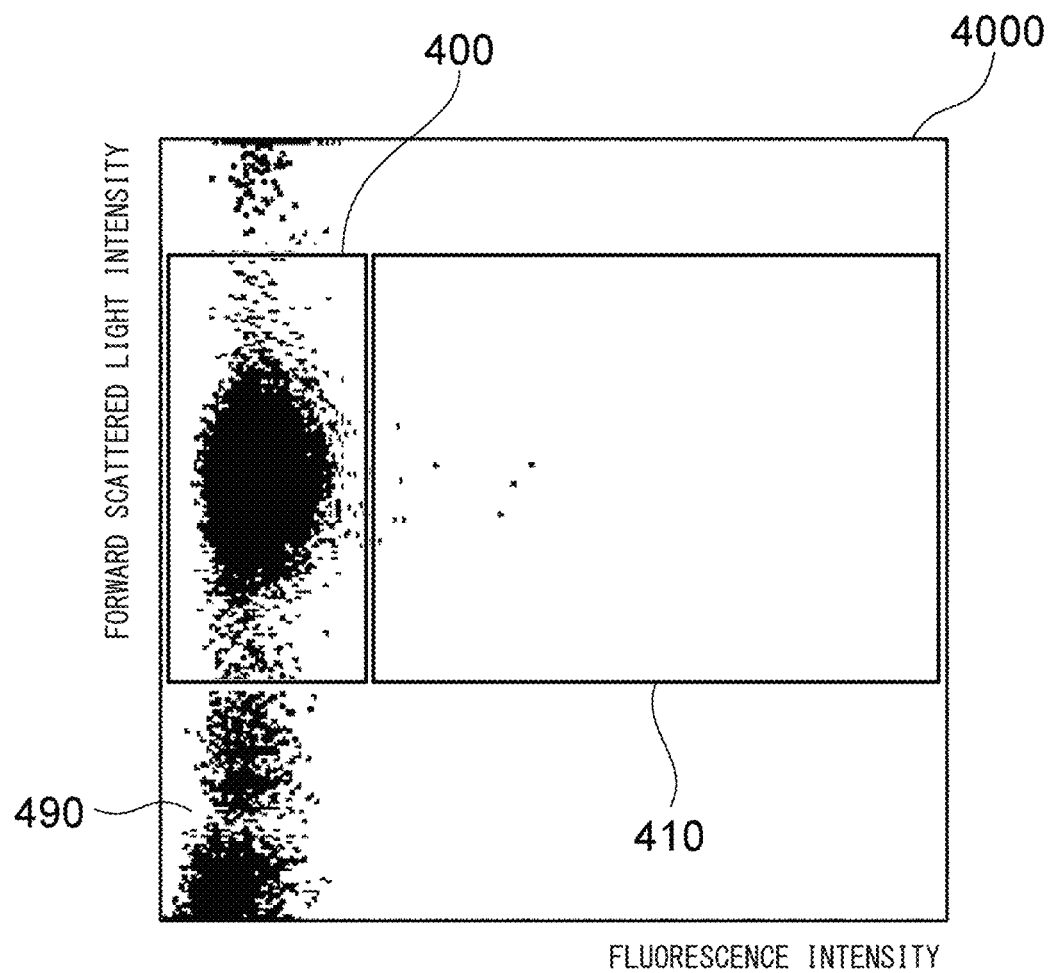
FIG. 16A illustrates an example of a scattergram representing a result of measurement of a normal sample, according to the embodiment.
Figure 16B:
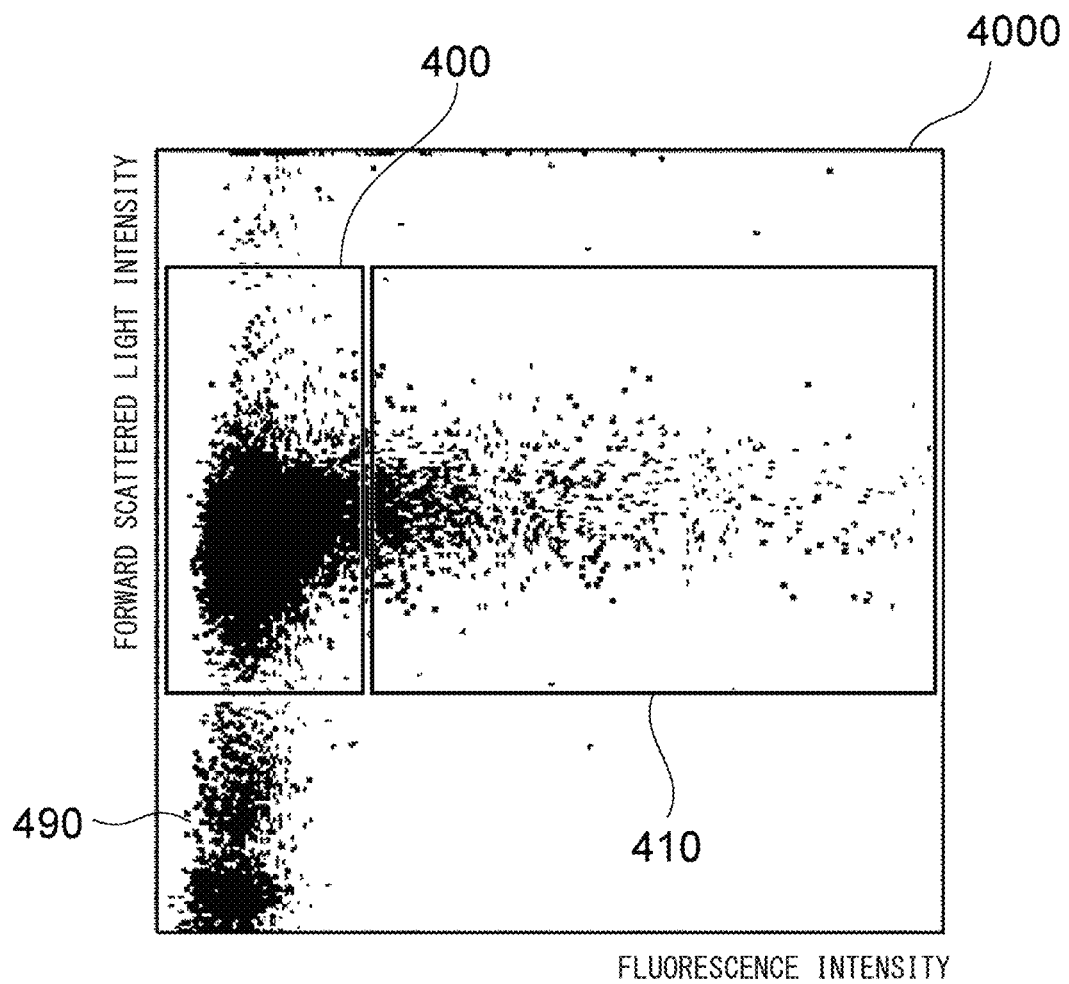
FIG. 16B illustrates an example of a scattergram representing a result of measurement of a blood sample collected from an iron-deficiency anemia patient, according to the embodiment.

FIG. 16A shows a result of measurement of a normal sample, that is, a blood sample collected from a healthy person. The number of particles appearing in the region 410 is small, and particles regarded as the intrinsically fluorescent red blood cells are hardly detected. Meanwhile, FIG. 16B shows a result of measurement of a blood sample (hereinafter, referred to as "iron-deficiency anemia sample") collected from an iron-deficiency anemia patient, and a lot of particles appear in the region 410 and a lot of particles regarded as intrinsically fluorescent red blood cells are detected.

Figure 16C:
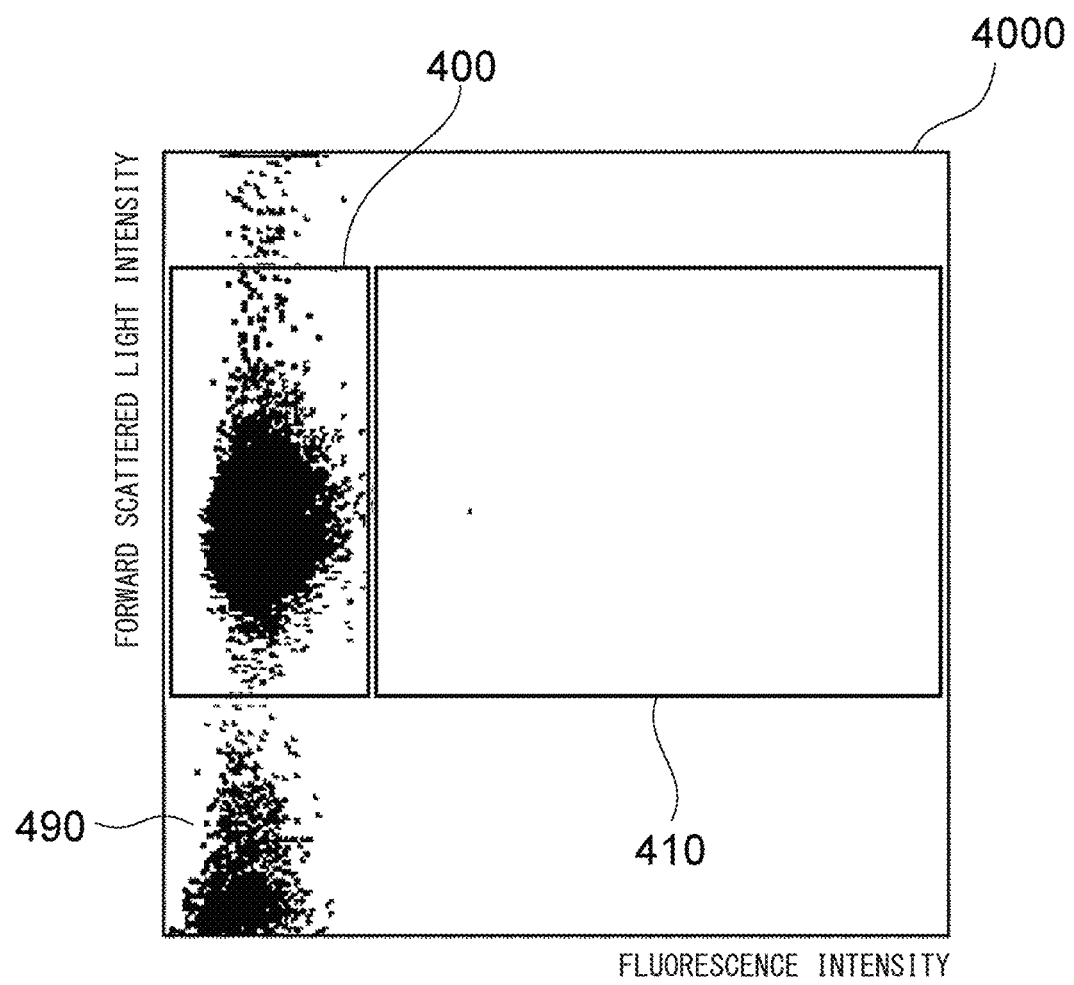
FIG. 16C illustrates an example of a scattergram representing a result of measurement of a blood sample collected from an α thalassemia patient, according to the embodiment.
Figure 16D:
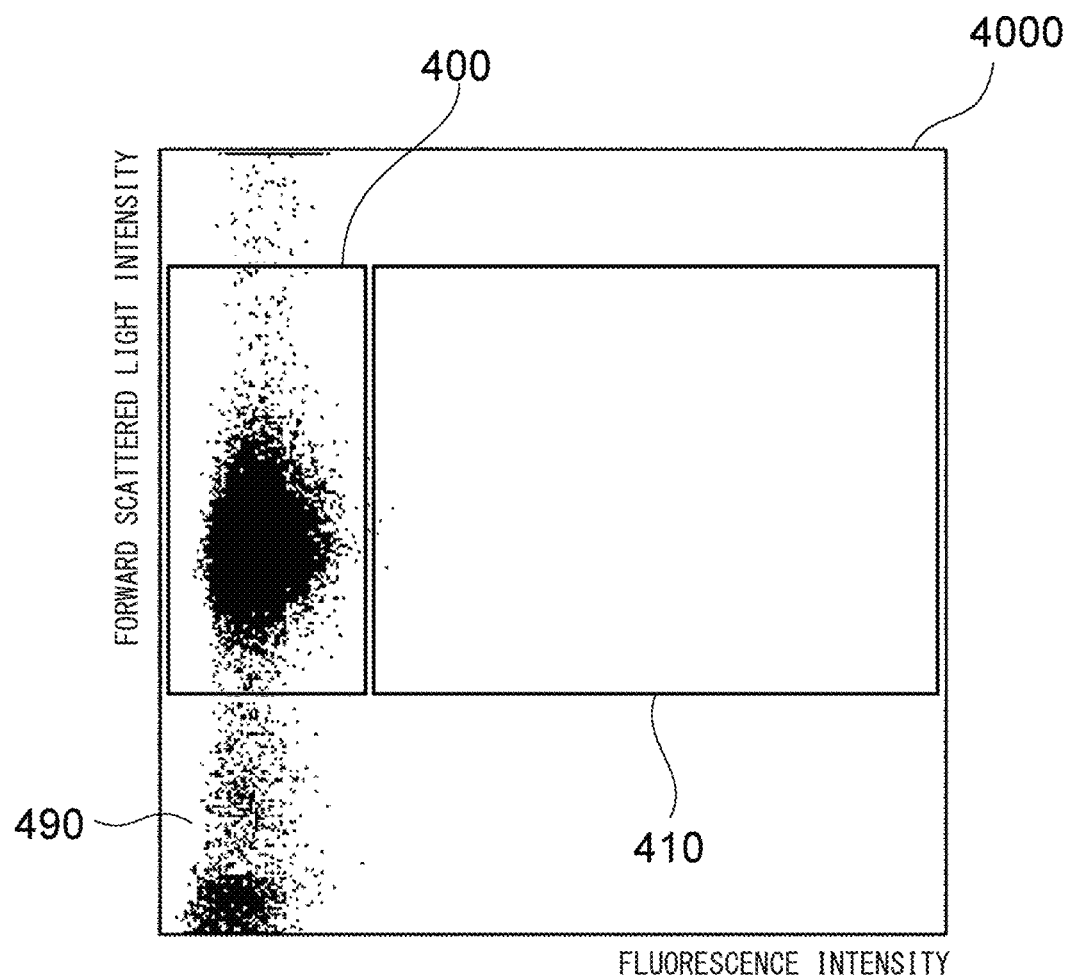
FIG. 16D illustrates an example of a scattergram representing a result of measurement of a blood sample collected from a β thalassemia patient, according to the embodiment.

FIG. 16C and FIG. 16D each show a result of measurement of a blood sample (hereinafter, referred to as "thalassemia sample") collected from a thalassemia patient, and the number of particles appearing in the region 410 is small, and particles regarded as intrinsically fluorescent red blood cells are hardly detected. Similarly to iron-deficiency anemia, thalassemia is classified as microcytic anemia and resembles iron-deficiency anemia in symptoms, a test value of a complete blood count (CBC) item, and the like. Therefore, possibility of iron-deficiency anemia is clinically preferably determined so as to be distinguished from thalassemia.

Returning to FIG. 15, in step S603, the CPU 301 calculates, as intrinsic fluorescence information, a ratio (hereinafter, referred to as "intrinsic fluorescence ratio") of the intrinsically fluorescent red blood cell number obtained in step S602 to the number of red blood cells counted in step S112 (FIG. 4). Instead of the number of red blood cells counted in step S112, the sum of the number of particles in the region 400 shown in FIG. 16A to FIG. 16D and the number of particles in the region 410 shown therein may be used as the number of red blood cells.

The CPU 301 determines, in step S604, whether or not the intrinsic fluorescence ratio is not less than a threshold value T7. The threshold value T7 is set such that, in a case where the intrinsic fluorescence ratio is not less than T7, iron-deficiency anemia can be determined as being likely to occur.

In a case where the intrinsic fluorescence ratio is not less than T7 (YES in step S604), the CPU 301 sets the iron-deficiency anemia determination flag as 1 in step S605, ends the second measurement data analysis process, and returns the process to the main routine. In a case where the intrinsic fluorescence ratio is less than T7 (NO in step S604), the CPU 301 maintains the iron-deficiency anemia determination flag as 0, ends the second measurement data analysis process, and returns the process to the main routine.

FIG. 4 is referred to again. The second measurement data analysis process as described above ends, and the CPU 301 then causes the display unit 310 to display the analysis result (step S115) and ends the process.

Figure 17:
FIG. 17 is a schematic diagram illustrating an example of display of an analysis result according to the embodiment.

An analysis result screen displayed on the display unit 310 will be described with reference to FIG. 17. An analysis result screen 500 includes a sample information display region 510, a patient information display region 520, a measurement result display region 530, and a reference information display region 540. The measurement result display region 530 includes a CBC item display region 531, a malaria item display region 532, and an intrinsic fluorescence item display region 533.

Information displayed in the sample information display region 510 represents a blood sample from which the analysis result displayed on the analysis result screen 500 has been obtained. In the patient information display region 520, information of a subject from which the blood sample is collected is displayed.

In the measurement result display region 530, measured values of the respective items which are obtained by the measurement data analysis process are displayed. In the CBC item display region 531, measured values of basic measurement items in blood cell analysis are displayed. The measured values displayed in the CBC item display region 531 include measured values of red blood cells (RBC) and white blood cells (WBC).

In the malaria item display region 532, measured values of measurement items for malaria-infected red blood cells are displayed. The measured values displayed in the malaria item display region 532 include the measured values of the number of malaria-infected red blood cells (M-RBC) counted in step S401, and the malaria-infected red blood cell ratio (MR) calculated in step S403. One of the number of malaria-infected red blood cells (M-RBC) or the malaria-infected red blood cell ratio (MR) may be displayed in the malaria item display region 532.

In the intrinsic fluorescence item display region 533, measured values of measurement items for intrinsic fluorescence are displayed. The measured values displayed in the intrinsic fluorescence item display region 533 include the measured values of the intrinsically fluorescent red blood cell number (AF-RBC) counted in step S602 and the intrinsic fluorescence ratio (AF) calculated in step S603. One of the intrinsically fluorescent red blood cell number (AF-RBC) or the intrinsic fluorescence ratio (AF) may be displayed in the intrinsic fluorescence item display region 533.

A message to be displayed in the reference information display region 540 is determined by a combination of the malaria species/stage determination flag and the iron-deficiency anemia determination flag. FIG. 18 illustrates a relationship between the combinations of both the flags and messages to be displayed. As illustrated in FIG. 18, in a case where each of the malaria species/stage determination flag and the iron-deficiency anemia determination flag represents 0, no message is displayed. In a case where the malaria species/stage determination flag represents 1 and the iron-deficiency anemia determination flag represents 0, "P. falciparum?" is displayed as a message indicating that falciparum malaria infection is suspected. In a case where the malaria species/stage determination flag represents 2 and the iron-deficiency anemia determination flag represents 0, "P. falciparum+" is displayed as a message indicating that falciparum malaria infection is highly likely to occur. In a case where the malaria species/stage determination flag represents 3 and the iron-deficiency anemia determination flag represents 0, "O. Malaria?" is displayed as a message indicating that malaria infection with a species other than falciparum malaria is suspected. In a case where the malaria species/stage determination flag represents 4 and the iron-deficiency anemia determination flag represents 0, "O. Malaria+" is displayed as a message indicating that malaria infection with a species other than falciparum malaria is highly likely to occur. In a case where the malaria species/stage determination flag represents any of 0 to 4 and the iron-deficiency anemia determination flag represents 1, "Iron deficiency?" is additionally displayed as a message indicating that iron-deficiency anemia is suspected. Furthermore, in a case where the malaria species/stage determination flag represents any of 1 to 4 and the iron-deficiency anemia determination flag represents 1, "Malaria & Iron alert" is additionally displayed as a flag indicating that iron preparation is to be carefully supplied to the patient. The flag allows an examiner to easily determine whether or not iron preparation is to be supplied to the patient.

In the blood analyzer according to the above-described embodiment, information used for determining whether or not iron preparation is to be supplied to an iron-deficiency anemia patient is generated by a single blood analyzer. Therefore, measurement for determining whether or not iron preparation is to be supplied to an iron-deficiency anemia patient can be facilitated.

EXAMPLE

Figure 19A:
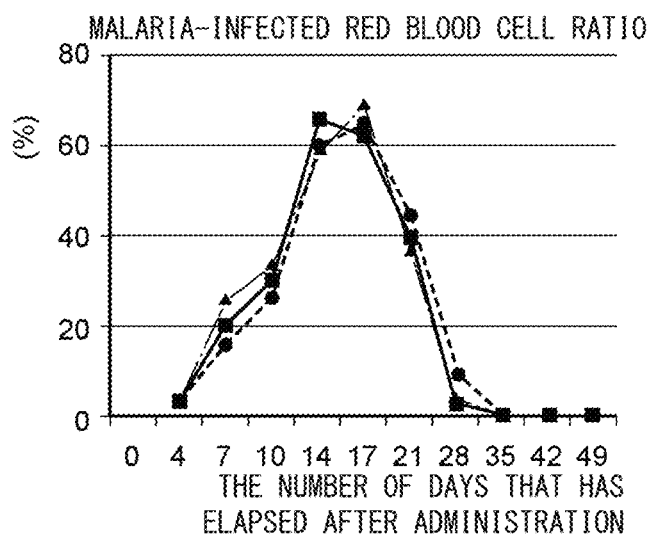
FIG. 19A illustrates a graph representing a ratio of the number of malaria-infected red blood cells in peripheral blood of a malaria-infected mouse, according to an example.
Figure 19B:
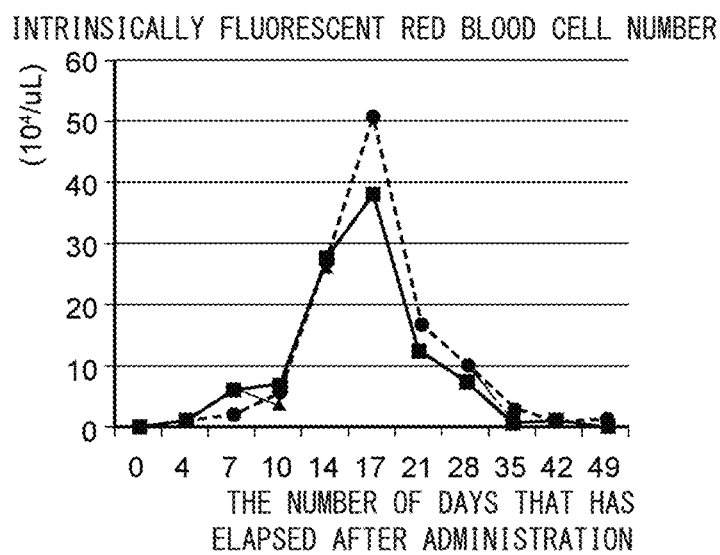
FIG. 19B illustrates a graph representing the intrinsically fluorescent red blood cell number, according to the example.
Figure 19C:
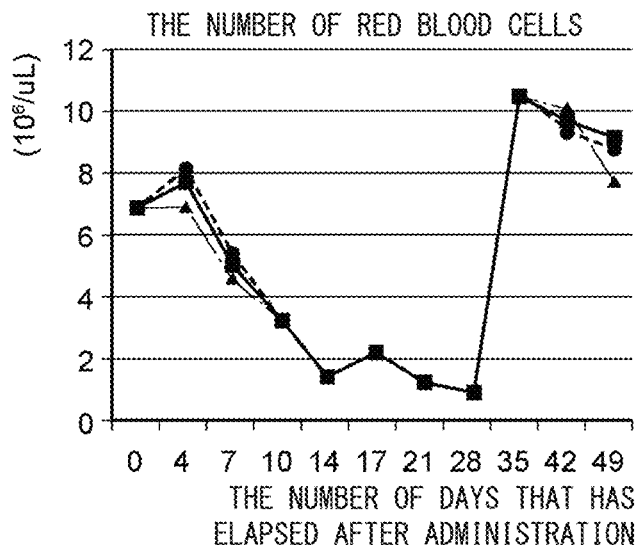
FIG. 19C illustrates a graph representing temporal change of the number of red blood cells, according to the example.

Red blood cells ($3\times10^5$ infected red blood cells/one mouse) infected with the nonlethal rodent *Plasmodium* strain *P. yoelii* 17XNL were administered into abdominal cavities of three C57BL/6 mice (female, 6 weeks old, purchased from Japan SLC, Inc.). On the fourth, the seventh, the tenth, the 14th, the 17th, the 21st, the 28th, the 35th, the 42nd, and the 49th days after that, mouse peripheral blood was collected, and the collected mouse peripheral blood was 50-fold diluted by PBS. Thereafter, an automatic multi-item blood cell analyzer XN-30 (manufactured by SYSMEX CORPORATION) was used to measure a ratio of the number of malaria-infected red blood cells to the total number of red blood cells, the intrinsically fluorescent red blood cell number, and the number of red blood cells. FIG. 19 shows the result. The automatic multi-item blood cell analyzer XN-30 has the same configuration as the optical detector unit 6.

Figure 20:
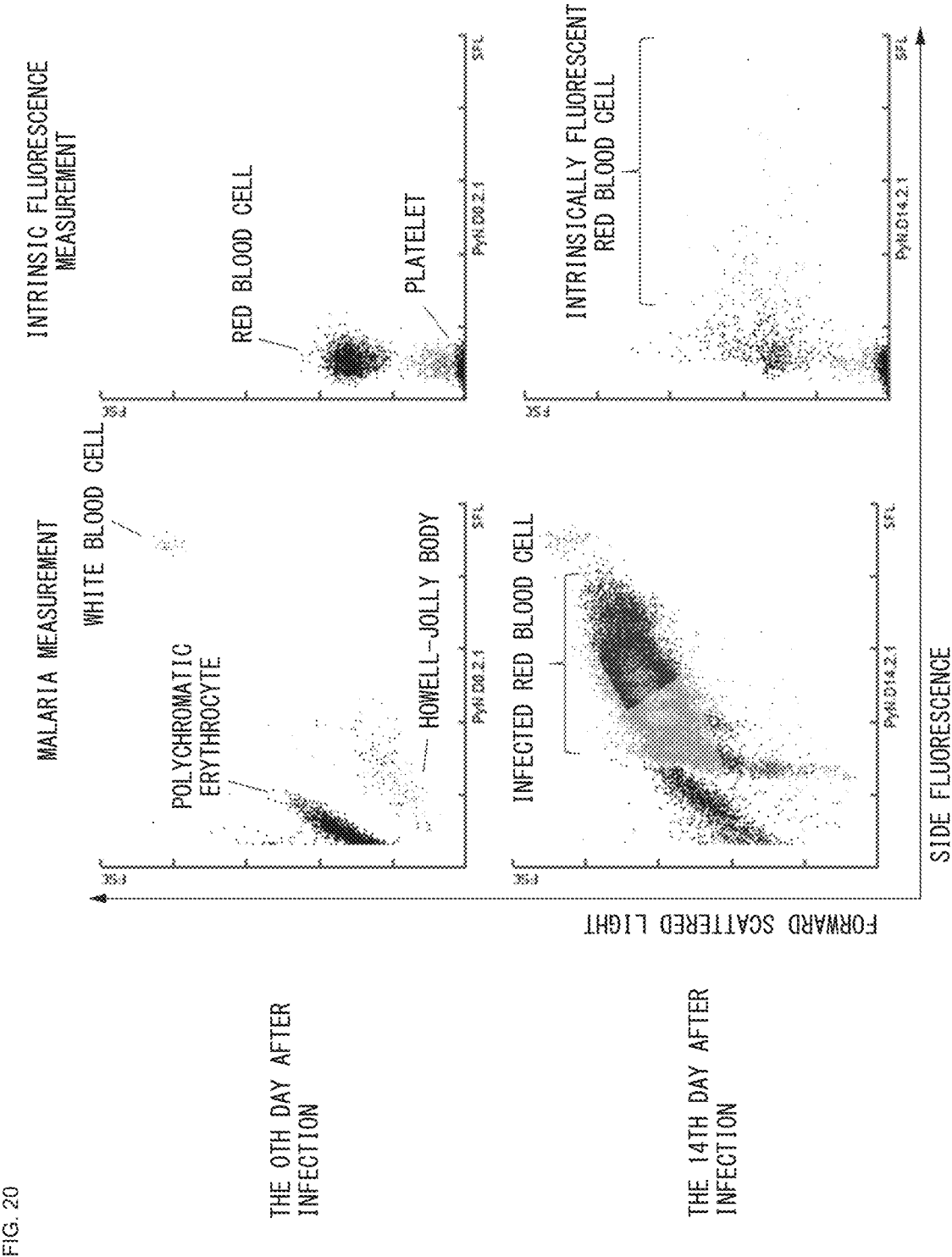
FIG. 20 illustrates scattergrams obtained by measuring a measurement sample prepared from peripheral blood of a malaria-infected mouse, according to the example.

On the 14th day after the infection, the ratio of the number of malaria-infected red blood cells to the total number of red blood cells was not less than 60%, and the intrinsically fluorescent red blood cell number was $50\times10^4$ red blood cells/μL corresponding to about 20% of the total number of red blood cells. FIG. 20 illustrates scattergrams on the 0th day after the infection and the 14th day after the infection. It is indicated that the infection increased red blood cells exhibiting staining fluorescence characteristics and scattered light characteristics specific to malaria infection, and increased red blood cells exhibiting intrinsic fluorescence characteristics specific to iron-deficiency anemia.

A BZ-X710 fluorescence microscope (KEYENCE) was used to observe fluorescence images of blood of a mouse which was infected with malaria and a mouse which was not infected with malaria. The observation was performed under conditions that a BZ-X GFP filter (Ex=470/40 nm, Em=525/50 nm, dichroic mirror=495 nm) was used in order to detect nucleic acid derived from *Plasmodium*, and a 5-ALA-405UF1-BLA filter (Ex=405/20 nm, Em=640/30 nm, dichroic mirror=425 nm) was used in order to detect protoporphyrin IX-specific fluorescence.

As a result, as shown in FIG. 21, both staining fluorescence derived from nucleic acid of *Plasmodium* and intrinsic fluorescence derived from protoporphyrin IX were not observed in the uninfected mouse. However, both fluorescence derived from a dye by which nucleic acid of *Plasmodium* was stained and intrinsic fluorescence derived from protoporphyrin IX were observed in the malaria-infected mouse. As a result, it was confirmed that the optical detector unit 6 of the blood analyzer according to the present embodiment was able to detect that malaria-infected red blood cells and protoporphyrin IX-containing red blood cells (iron-deficient red blood cells) were in a malaria-infected mouse.

What is claimed is:

1. A blood analyzer comprising:
   a first sample preparation unit configured to prepare, from a blood sample, a first measurement sample for measuring a red blood cell infected with malaria;
   a second sample preparation unit configured to prepare, from the blood sample, a second measurement sample for measuring intrinsic fluorescence of a red blood cell, the first sample preparation unit being physically separated from the second sample preparation unit;
   a suction unit configured to suction the blood sample from a sample container that stores the blood sample through a suction tube, the suction unit being configured to move the suction tube to the first sample preparation unit and the second sample preparation unit respectively, the suction unit being configured to supply the blood sample to the first sample preparation unit and the second sample preparation unit respectively;
   a light source unit configured to apply light to the first measurement sample and the second measurement sample;
   a detection unit configured to detect fluorescence and scattered light generated from the first measurement sample to which light has been applied, and detect intrinsic fluorescence generated from the second measurement sample to which light has been applied; and
   an information processing unit configured to generate information about malaria infection based on fluorescence and scattered light detected from the first measurement sample, and generate information about iron-deficiency anemia based on intrinsic fluorescence detected from the second measurement sample.

2. The blood analyzer of claim 1, wherein the first sample preparation unit mixes the blood sample, a hemolyzing agent for contracting a red blood cell, and a nucleic acid staining dye, to prepare the first measurement sample.

3. The blood analyzer of claim 1, wherein the second sample preparation unit mixes the blood sample, and a diluent that does not contain neither a hemolyzing agent for contracting a red blood cell nor a nucleic acid staining dye, to prepare the second measurement sample.

4. The blood analyzer of claim 1, wherein
the first sample preparation unit and the second sample preparation unit prepare the first measurement sample and the second measurement sample, respectively, from a part of the blood sample suctioned by the suction unit.

5. The blood analyzer of claim 1, wherein the light source unit emits light in a band of a wavelength that is not less than 400 nm and not greater than 435 nm.

6. The blood analyzer of claim 1, further comprising a flow cell in which the first and the second measurement samples flow, wherein
the light source unit is configured to apply light to the first and the second measurement samples flowing in the flow cell, and
the detector is configured to detect fluorescence and scattered light generated from the first measurement sample flowing in the flow cell, and detect intrinsic fluorescence generated from the second measurement sample flowing in the flow cell.

7. The blood analyzer of claim 6, further comprising a washing unit configured to wash the flow cell after one of the first and the second measurement samples has passed through the flow cell and before the other of the first and the second measurement samples passes through the flow cell.

8. The blood analyzer of claim 1, wherein the information processing unit outputs display information for simultaneously outputting, to a display unit, the information about malaria infection and the information about iron-deficiency anemia.

9. The blood analyzer of claim 1, wherein the information about malaria infection includes a number of malaria-infected red blood cells or a ratio of the number of malaria-infected red blood cells to a number of red blood cells.

10. The blood analyzer of claim 1, wherein the information about malaria infection includes information indicating possibility of malaria infection based on a result of comparison between a number of malaria-infected red blood cells or a ratio of the number of malaria-infected red blood cells to a number of red blood cells, and a threshold value for determining possibility of malaria infection.

11. The blood analyzer of claim 10, wherein the information indicating possibility of malaria infection includes information indicating a species of malaria that has caused infection.

12. The blood analyzer of claim 1, wherein the information about iron-deficiency anemia includes a number of red blood cells that generate intrinsic fluorescence, or a ratio of the number of red blood cells that generate intrinsic fluorescence, to a number of red blood cells.

13. The blood analyzer of claim 1, wherein the information about iron-deficiency anemia includes information indicating possibility of iron-deficiency anemia based on a result of comparison between a number of red blood cells that generate intrinsic fluorescence or a ratio of the number of red blood cells that generate intrinsic fluorescence, to a number of red blood cells, and a threshold value for determining possibility of iron-deficiency anemia.

14. The blood analyzer of claim 1, wherein
the information about malaria infection includes a result of comparison between a number of malaria-infected red blood cells or a ratio of the number of malaria-infected red blood cells to a number of red blood cells, and a threshold value for determining possibility of malaria infection,
the information about iron-deficiency anemia includes a result of comparison between a number of red blood cells that generate intrinsic fluorescence or a ratio of the number of red blood cells that generate intrinsic fluorescence, to a number of red blood cells, and a threshold value for determining possibility of iron-deficiency anemia, and
the information processing unit generates an alerting flag in a case where the result of the comparison with the threshold value for determining possibility of malaria infection indicates that malaria infection is likely to occur, and the result of the comparison with the threshold value for determining possibility of iron-deficiency anemia indicates that iron-deficiency anemia is likely to occur.

15. An information processing apparatus for generating information about malaria infection and information about iron-deficiency anemia, the information processing apparatus comprising a controller, wherein
the controller
is connected to a detection unit for detecting fluorescence and scattered light generated by applying light to a first measurement sample for measuring a red blood cell infected with malaria, and detecting intrinsic fluorescence generated by applying light to a second measurement sample for measuring intrinsic fluorescence of a red blood cell,
is connected to a suction unit configured to suction a blood sample from a sample container that stores the blood sample through a suction tube, wherein the suction unit is configured to move the suction tube to a first sample preparation unit and a second sample preparation unit respectively, the first sample preparation unit is physically separated from the second sample preparation unit, wherein the suction unit is configured to supply the blood sample to the first sample preparation unit and the second sample preparation unit respectively, and wherein the first sample preparation unit is configured to prepare the first measurement sample and the second sample preparation unit is configured to prepare the second measurement sample, and
is programed to generate the information about malaria infection based on the detected fluorescence and scattered light from the first measurement sample, and generate the information about iron-deficiency anemia based on the intrinsic fluorescence detected from the second measurement sample.

16. The information processing apparatus of claim 15, further comprising a display unit, wherein
the controller is programed to output display information for simultaneously outputting, to the display unit, the information about malaria infection and the information about iron-deficiency anemia.

17. The information processing apparatus of claim 15, wherein
- the information about malaria infection includes a result of comparison between a number of malaria-infected red blood cells, or a ratio of the number of malaria-infected red blood cells to a number of red blood cells, and a threshold value for determining possibility of malaria infection, and
- the information about iron-deficiency anemia includes a result of comparison between a number of red blood cells that generate intrinsic fluorescence, or a ratio of the number of red blood cells that generate intrinsic fluorescence, to a number of red blood cells, and a threshold value for determining possibility of iron-deficiency anemia, and
- the controller is programmed to generate an alerting flag in a case where the result of the comparison with the threshold value for determining possibility of malaria infection indicates that malaria infection is likely to occur, and the result of the comparison with the threshold value for determining possibility of iron-deficiency anemia indicates that iron-deficiency anemia is likely to occur.

18. A non-transitory computer-readable medium storing instructions for controlling an information processing apparatus that generates information about malaria infection and information about iron-deficiency anemia, wherein
- the information processing apparatus is connected to a detection unit for detecting fluorescence and scattered light generated by applying light to a first measurement sample for measuring a red blood cell infected with malaria, and detecting intrinsic fluorescence generated by applying light to a second measurement sample for measuring intrinsic fluorescence of a red blood cell,
- the information processing apparatus is connected to a suction unit configured to suction a blood sample from a sample container that stores the blood sample through a suction tube, wherein the suction unit is configured to move the suction tube to a first sample preparation unit and a second sample preparation unit respectively, the first sample preparation unit is physically separated from the second sample preparation unit, wherein the suction unit is configured to supply the blood sample to the first sample preparation unit and the second sample preparation unit respectively, and wherein the first sample preparation unit is configured to prepare the first measurement sample and the second sample preparation unit is configured to prepare the second measurement sample, and
- the instructions are configured to cause the information processing apparatus to perform:
- generating the information about malaria infection based on the detected fluorescence and scattered light from the first measurement sample; and
- generating the information about iron-deficiency anemia based on the intrinsic fluorescence detected from the second measurement sample.

19. The non-transitory computer-readable medium of claim 18, further causing the information processing apparatus to output display information for simultaneously outputting, to a display unit, the information about malaria infection and the information about iron-deficiency anemia.

20. The non-transitory computer-readable medium of claim 18, wherein
- the information about malaria infection includes a result of comparison between a number of malaria-infected red blood cells, or a ratio of the number of malaria-infected red blood cells to a number of red blood cells, and a threshold value for determining possibility of malaria infection,
- the information about iron-deficiency anemia includes a result of comparison between a number of red blood cells that generate intrinsic fluorescence, or a ratio of the number of red blood cells that generate intrinsic fluorescence, to a number of red blood cells, and a threshold value for determining possibility of iron-deficiency anemia, and
- the instructions are configured to further cause the information processing apparatus to generate an alerting flag in a case where the result of the comparison with the threshold value for determining possibility of malaria infection indicates that malaria infection is likely to occur, and the result of the comparison with the threshold value for determining possibility of iron-deficiency anemia indicates that iron-deficiency anemia is likely to occur.

\* \* \* \* \*